United States Patent
Kang et al.

(10) Patent No.: US 11,820,961 B2
(45) Date of Patent: *Nov. 21, 2023

(54) MUSK COMPOSITIONS AND METHODS OF USE THEREOF

(71) Applicant: Takasago International Corporation, Tokyo (JP)

(72) Inventors: Raphael K. L. Kang, Leonia, NJ (US); Alba T. Cilia, Township of Washington, NJ (US)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 145 days.

This patent is subject to a terminal disclaimer.

(21) Appl. No.: 17/209,056

(22) Filed: Mar. 22, 2021

(65) Prior Publication Data

US 2021/0277328 A1  Sep. 9, 2021

Related U.S. Application Data

(63) Continuation of application No. 15/197,747, filed on Jun. 29, 2016, now Pat. No. 10,988,706.

(60) Provisional application No. 62/186,240, filed on Jun. 29, 2015.

(51) Int. Cl.
| | |
|---|---|
| *C11B 9/00* | (2006.01) |
| *A61Q 13/00* | (2006.01) |
| *A61Q 5/02* | (2006.01) |
| *A61Q 15/00* | (2006.01) |
| *A61K 8/34* | (2006.01) |
| *A61K 8/35* | (2006.01) |
| *A61K 8/37* | (2006.01) |
| *A61K 8/49* | (2006.01) |
| *A61K 31/045* | (2006.01) |
| *A61K 31/122* | (2006.01) |
| *A61K 31/215* | (2006.01) |
| *A61K 31/23* | (2006.01) |
| *A61K 31/365* | (2006.01) |
| *A61K 31/12* | (2006.01) |

(52) U.S. Cl.
CPC ............ *C11B 9/0084* (2013.01); *A61K 8/342* (2013.01); *A61K 8/35* (2013.01); *A61K 8/37* (2013.01); *A61K 8/4973* (2013.01); *A61K 31/045* (2013.01); *A61K 31/12* (2013.01); *A61K 31/122* (2013.01); *A61K 31/215* (2013.01); *A61K 31/23* (2013.01); *A61K 31/365* (2013.01); *A61Q 5/02* (2013.01); *A61Q 13/00* (2013.01); *A61Q 15/00* (2013.01); *C11B 9/0015* (2013.01); *C11B 9/0019* (2013.01); *C11B 9/0034* (2013.01); *C11B 9/0061* (2013.01)

(58) Field of Classification Search
CPC .... C11B 9/0019; C11B 9/0034; C11B 9/0061
See application file for complete search history.

(56) References Cited

U.S. PATENT DOCUMENTS

| | | | |
|---|---|---|---|
| 2,438,091 A | 3/1948 | Lynch | |
| 2,528,378 A | 10/1950 | Mannheimer | |
| 2,658,072 A | 11/1953 | Milton | |
| 2,809,971 A | 10/1957 | Jack et al. | |
| 3,236,733 A | 2/1966 | Karsten et al. | |
| 3,753,196 A | 8/1973 | Kurtz et al. | |
| 3,761,418 A | 9/1973 | Parran | |
| 3,792,068 A | 2/1974 | Luedders et al. | |
| 3,887,692 A | 6/1975 | Gilman et al. | |
| 3,904,741 A | 9/1975 | Jones et al. | |
| 4,049,792 A | 9/1977 | Elsnau | |
| 4,120,948 A | 10/1978 | Shelton | |
| 4,323,683 A | 4/1982 | Bolich, Jr. et al. | |
| 4,345,080 A | 8/1982 | Bolich, Jr. et al. | |
| 4,359,456 A | 11/1982 | Gosling et al. | |
| 4,379,753 A | 4/1983 | Bolich, Jr. | |
| 4,470,982 A | 9/1984 | Winkler | |
| 4,985,238 A | 1/1991 | Tanner et al. | |
| 5,019,375 A | 5/1991 | Tanner et al. | |
| 5,104,646 A | 4/1992 | Bolich, Jr. et al. | |
| 5,106,609 A | 4/1992 | Bolich, Jr. et al. | |
| 5,429,816 A | 7/1995 | Hofrichter et al. | |
| 5,714,137 A | 2/1998 | Trinh et al. | |
| 5,879,584 A | 3/1999 | Bianchetti et al. | |
| 5,891,424 A | 4/1999 | Bretzler et al. | |
| 5,942,217 A | 8/1999 | Woo et al. | |
| 5,976,514 A | 11/1999 | Guskey et al. | |
| 6,034,052 A | 3/2000 | Körber et al. | |
| 6,488,943 B1 | 12/2002 | Beerse et al. | |
| 6,869,923 B1 | 3/2005 | Cunningham et al. | |
| 7,968,606 B2 | 6/2011 | Warr et al. | |

(Continued)

FOREIGN PATENT DOCUMENTS

| | | |
|---|---|---|
| BE | 825146 A1 | 8/1975 |
| CA | 1 164 347 A | 3/1984 |

(Continued)

OTHER PUBLICATIONS

U.S. Appl. No. 15/197,752, (2016/0376524), filed Jun. 29, 2016 (Dec. 29, 2016).
U.S. Appl. No. 16/692,730 (2020/0332222), filed Oct. 22, 2020 (Oct. 22, 2020).
U.S. Appl. No. 15/197,752, May 24, 2019 Non-Final Office Action.
U.S. Appl. No. 16/692,730, Feb. 1, 2021 Response to Restriction Requirement.
U.S. Appl. No. 16/692,730, Feb. 19, 2021 Non-Final Office Action.
U.S. Appl. No. 16/692,730, Jul. 31, 2020 Restriction Requirement.
Bensafi et al., "Autonomic Nervous System Responses to Odours: the Role of Pleasantness and Arousal," Chemical Senses 27:703-709 (2002).

(Continued)

*Primary Examiner* — Michael P Cohen
(74) *Attorney, Agent, or Firm* — Baker Botts L.L.P

(57) ABSTRACT

A fragrance composition comprising one or more musk or fragrance accords for use in reducing or inhibiting a subject's physiological reaction to stress. The composition can be incorporated into consumer products.

13 Claims, 12 Drawing Sheets

(56) References Cited

U.S. PATENT DOCUMENTS

| | | |
|---|---|---|
| 2004/0033279 A1 | 2/2004 | Warrenberg et al. |
| 2005/0153852 A1 | 7/2005 | Evans et al. |
| 2005/0245407 A1 | 11/2005 | Ishihara et al. |
| 2005/0276831 A1 | 12/2005 | Dihora et al. |
| 2006/0165622 A1 | 7/2006 | Hiramoto et al. |
| 2006/0270587 A1 | 11/2006 | Shoji et al. |
| 2007/0003499 A1 | 1/2007 | Shen et al. |
| 2007/0020263 A1 | 1/2007 | Shitara et al. |
| 2007/0275866 A1 | 11/2007 | Dykstra |
| 2010/0009285 A1 | 1/2010 | Daems et al. |
| 2010/0287710 A1 | 11/2010 | Denutte et al. |
| 2010/0322878 A1 | 12/2010 | Stella et al. |
| 2011/0152146 A1 | 6/2011 | Denutte et al. |
| 2012/0015058 A1 | 1/2012 | Lee et al. |
| 2012/0219610 A1 | 8/2012 | Smith, III et al. |
| 2013/0102981 A1 | 4/2013 | Perring et al. |
| 2014/0194338 A1 | 7/2014 | Behan et al. |

FOREIGN PATENT DOCUMENTS

| | | | |
|---|---|---|---|
| CA | 2 753 315 A1 | 5/2006 | |
| CN | 102764280 A | 11/2012 | |
| EP | 1293554 A1 * | 3/2003 | ............ A61K 8/922 |
| EP | 2 184 339 A1 | 5/2010 | |
| GB | 1 347 950 A | 2/1974 | |
| GB | 2 048 229 A | 12/1980 | |
| GB | 2 144 992 A | 3/1985 | |
| JP | 2005-029776 A | 2/2005 | |
| KR | 2004-056622 A | 7/2004 | |
| WO | WO 03/037841 A1 | 5/2003 | |

OTHER PUBLICATIONS

Crepaldi et al., "Chemical, Structural, and Thermal Properties of Zn(II)-Cr(III) Layered Double Hydroxides Intercalated with Sulfated and Sulfonated Surfactants," J Colloid and Interface Sci. 248:429-442 (2002).

Feicht et al., "Evaluation of a Seven-Week Web-Based Happiness Training to Improve Psychological Well-Being, Reduce Stress, and Enhance Mindfulness and Flourishing: A Randomized Controlled Occupational Health Study," Evidence-Based Complementary and Alternative Medicine vol. 2013, Art. ID 676953, pp. 1-14 (2013).

Fukui et al., "The effects of odor on cortisol and testosterone in healthy adults," Neuroendocrinology Letters 28(4):433-437 (2007).

Fukui et al., "The effects of odor on cortisol and testosterone in healthy adults." Neuroendocrinology Letters, vol. 28 No. 4 2007, 101-105 (Year: 2007).

Fukui, "Influence of odor on the human body—human pheromone, steroids and behavioral endocrinological study," Aroma Research 11(1):79-83 (2010) (with English Abstract).

Gordis et al., "Interparental aggression and parent-adolescent salivary alpha amylase symmetry," Physiology & Behavior, 100:225-233 (2010).

Gordis et al., "Salivary alpha amylase-cortisol asymmetry in maltreated youth," Hormones and Behavior, 53:96-103 (2008).

Granger et al., "Salivary a-Amylase in Biobehavioral Research: Recent Developments and Applications," Ann. NY Acad. Sci., 1098:122-144 (2007).

Herrmann, "The Chemistry and Biology of Volatiles," Chichester UK 2010: John Wiley and Sons, Section 7.3.4 (Year: 2010).

International Search Report and Written Opinion dated Aug. 24, 2016 in International Application No. PCT/US2016/040223.

International Search Report and Written Opinion dated Sep. 9, 2016 in International Application No. PCT/US2016/040224.

Jellinek (The Psychological Basis of Perfumery, 4th Edition. London: Chapman and Hall, 1997, p. 41) (Year: 1997).

Keller et al., "Salivary alpha-amylase as a longitudinal predictor of children's externalizing symptoms: Respiratory sinus arrhythmia as a moderator of effects," Psychoneuroendocrinology, 34:633-643 (2009).

Kirchhoff et al., "DEPARTMENTS-Chemscripts-Formulating a synthetic perfume—Rapidly" Chemical Innovation 30.11 (2000): 52-53 (Year: 2000).

Komori, "Anti-stress and antidepressant effects of fragrances and autonomic nervous system," Aroma Research 9(3):202-207 (2008) (with English abstract).

Morioka et al., "Effects of Zinc on the New Preparation Method of Hydroxy Double Salts," Inorg. Chem. 38:4211-4216 (1999).

"Musk Acetate." Accessed Jul. 9, 2019 from https://web.archive.org/web/20120121030019/http://www.thegoodscentscompany.com/data/rwl005121. html; dated Jan. 21, 2012), (Year: 2012).

Nater et al., "Salivary alpha-amylase as a non-invasive biomarker for the sympathetic nervous system: Current state of research," Psychoneuroendocrinology, 34:486-496 (2009).

Nishimura et al., "Effect of Neroli Scent on Mental Stress Loads," Aromatopia 95:12-14 (2009) (with English translation).

Okazaki et al., "The Odour of Glandular Secretion and Human Emotion-Animal Perfume Materials and Human Body Odour Related Chemicals," Proceedings of the 13th International Congress of Flavours, Fragrances and Essential Oils, Istanbul, Turkey, vol. 3, Oct. 15-19, 1995.

Proctor et al., "Regulation of salivary gland function by autonomic nerves," Autonomic Neuroscience: Basic and Clinical 133:3-18 (2007).

Sawabe et al., "About the estrogenic activity and the stress reduction and a relaxation effect of odor after stress loading," Aroma Research 13(1):58-63 (2012) (with English abstract).

Scifinder search for 1,4-dioxacyclohexadecane-5, 16-dione. Dated Apr. 2, 2020. (Year: 2020).

Soo-Quee Koh et al., "The Use Of Salivary Biomarkers In Occupational And Environmental Medicine," Occup Environ Med 64:202-210 (2007).

Stress and rosamusk perfume—google scholar search Feb. 13, 2021 (Year: 2021).

Stress and musk perfume—google scholar search—Feb. 13, 2021 (Year: 2021).

Taverniers et al., "Force-on-Force Handgun Practice: An Intra-Individual Exploration of Stress Effects, Biomarker Regulation, and Behavioral Changes," Human Factors 56(2):403-413 (2014).

Todd et al., "Volatile Silicone Fluids for Cosmetic Formulations," Cosmetics and Toiletries, 91:28-32 (Jan. 1976).

Van Stegeren et al., "Salivary alpha amylase as marker for adrenergic activity during stress: Effect of betablockade," Psychoneuroendocrinology, 31:137-141 (2006).

Vernet-Maury et al., "Basic emotions induced by odorants: a new approach based on autonomic pattern results," Journal of the Autonomic Nervous System 75:176-183 (1999).

Warrenburg, "Measurement of Emotion in Olfactory Research," ACS Symposium Series 825(Chemistry of Taste):243-260 (2002).

Wells A.F., "Structural Inorganic Chemistry" Clarendon Press, Table of Contents (1975).

Wong et al., "Job Strain and Shift Work Influences on Biomarkers and Subclinical Heart Disease Indicators: A Pilot Study," J Occup Environ Hyg. 9(8):467-477 (2012).

Zauber et al., "Dynamics of salivary proteins and metabolites during extreme endurance sports—a case study," Proteomics 12:2221-2235 (2012).

* cited by examiner

MUSK COMPOSITIONS AND METHODS OF USE THEREOF

CROSS-REFERENCE TO RELATED APPLICATIONS

This application is a continuation of U.S. patent application Ser. No. 15/197,747, filed Jun. 29, 2016, which claims priority to U.S. Provisional Application No. 62/186,240, filed Jun. 29, 2015, both of which are incorporated by reference herein in their entireties.

FIELD

The present disclosure relates to fragrance compositions comprising one or more musk or fragrance accords. The compositions can be administered to reduce or inhibit a subject's response to stress.

BACKGROUND

Stress is the human body's reaction to internal or external stimuli. It is well documented that stress typically causes a negative impact on a person's mental and physical health. Mental and physical symptoms of stress may include, but are not limited to, moodiness, irritability or short temper, agitation, inability to relax, general unhappiness, aches and pains, diarrhea or constipation, indigestion, nausea, dizziness, chest pain, and/or rapid heartbeat. Long-term, or chronic stress has been linked to anxiety, depression, heart problems, weight gain, sleep disorders, and memory and concentration impairment. Numerous pharmaceutical remedies exist to treat or lessen these stress responses, however there remains a need for alternative remedies and solutions.

Aromatherapy is a known practice for treating stress and promoting relaxation using essential oils. However, fragrances comprise a variety of compounds, which can lose their individual scent identity when combined with other compounds. With such mixtures, it can be difficult for consumers to elucidate which particular compounds are effective for stress reduction. Therefore, there remains a need to identify fragrance accords that actually impact an individual's reaction to stress. The present disclosure addresses this need in further detail below.

SUMMARY OF THE INVENTION

The present disclosure relates to fragrance compositions comprising at least one compound that effectively reduces or inhibits physiological responses to stress. Specifically, the present disclosure is directed to compositions comprising at least one musk accord and a method of using such compositions to reduce or inhibit a subject's response to stress.

In certain embodiments, the presently disclosed subject matter provides for fragrance compositions comprising at least one musk accord, wherein the musk accord comprises at least one musk compound selected from the group consisting of 1-(3,3-dimethylcyclohexyl)ethyl acetate, ((12E)-1-oxacyclohexadec-12-en-2-one), 17-oxacycloheptadec-6-en-1-one, L-Muscone, 3-methyl-5-((1R)-2,2,3-trimethylcyclopentyl)pentan-2-one, 1-(1,1,2,3,3,6-hexamethyl-2H-inden-5-yl)ethanone, ((E)-2-methyl-4-(2,2,3-trimethyl-1-cyclopent-3-enyl)but-2-en-1-ol), and combinations thereof, wherein the musk accord is present in an amount of from about 1% to about 100% by weight of the fragrance composition. In certain embodiments, the musk accord is present in an amount of at least about 5% w/w, or at least about 10% w/w, or at least about 20% w/w.

The presently disclosed subject matter further provides consumer products comprising the fragrance compositions as disclosed herein. In certain embodiments, the consumer product comprises a sufficient amount of the at least one musk accord to provide a concentration of said at least one musk of at least 7 nanograms per cubic foot of air, preferably from about 7.4 nanograms per cubic foot of air to about 28 nanograms per cubic foot of air, more preferably 7.4 nanograms per cubic foot of air to about 27.7 nanograms per cubic foot of air, said consumer product being a hair removal, sexual health care, fine fragrance and/or pet care product.

In certain embodiments, the consumer product further comprises, in addition to said at least one musk accord, one or more fragrance raw materials. In certain embodiments, the consumer product further comprises an ingredient selected from the group consisting of bleach activators, hydrogen peroxide, perfumes, fragrance delivery systems, carriers, structurants, solvents, and mixtures thereof.

The presently disclosed subject matter further provides for methods of reducing or inhibiting a stress response in a subject in need thereof comprising: administering the fragrance composition disclosed herein to the subject in an amount effective to reduce or inhibit a response to stress stimuli. In certain embodiments, the fragrance composition is administered before, during, or after exposure to the stress stimuli.

DETAILED DESCRIPTION

Figure 1:
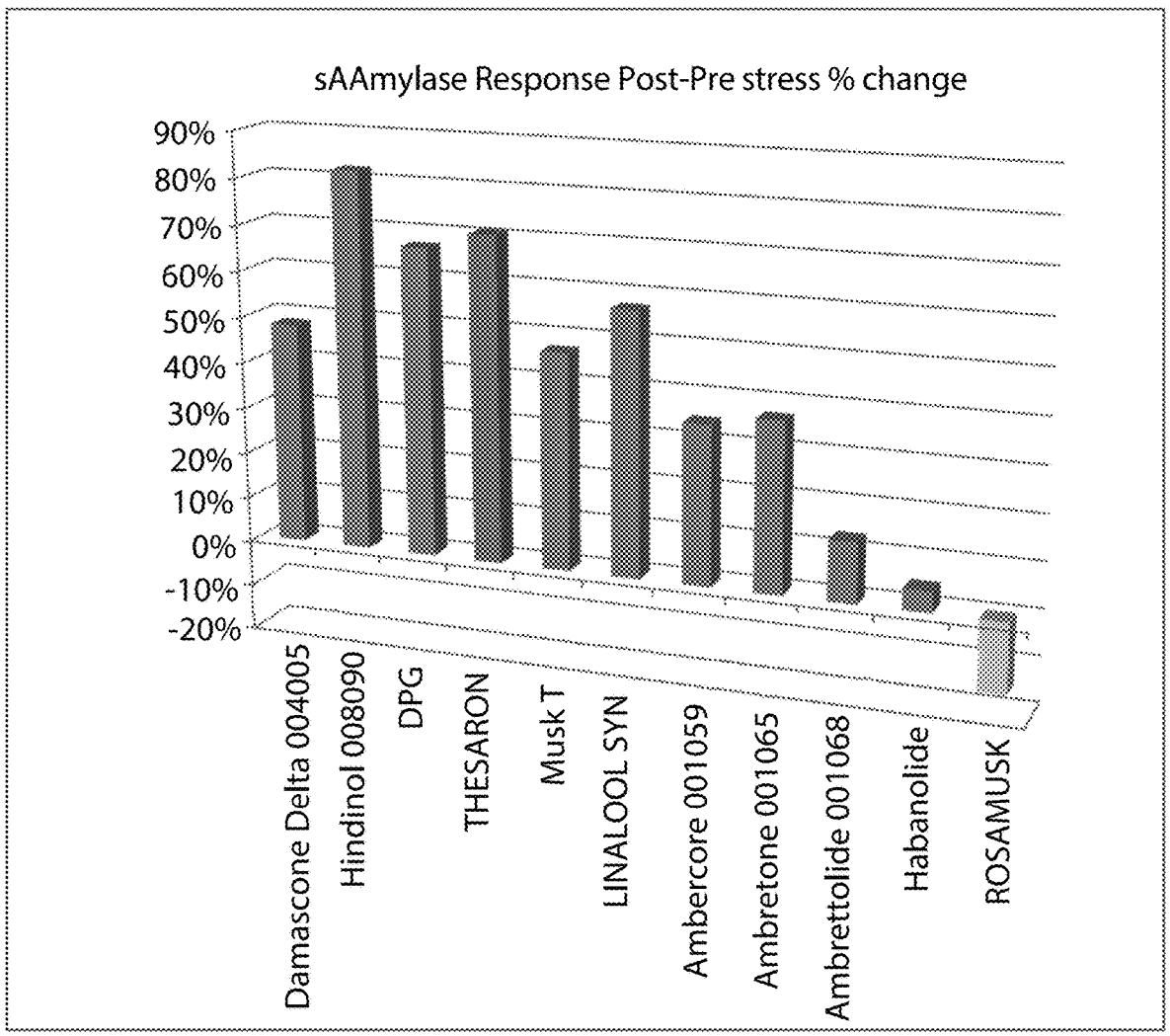
FIG. 1 provides a graphical analysis of a subject's levels of salivary alpha-amylase, measured before and after exposure to a stressor. In the graphic, each compound tested is provided (x-axis), and the change in salivary alpha-amylase, measured before and after exposure to a stressor, is evaluated on a percent scale (y-axis).

As discussed above, there is a need in the art to determine which fragrances and which accords within a fragrance impact a subject's reaction to stress so as to formulate an effective composition for treatment thereof. The presently disclosed subject matter addresses this need through a fragrance composition comprising at least one musk accord which can be administered to a subject before, during, or after exposure to a stressor to effectively reduce or inhibit stress.

1. Definitions

The terms used in this specification generally have their ordinary meanings in the art, within the context of this disclosure and in the specific context where each term is used. Certain terms are discussed below, or elsewhere in the specification, to provide additional guidance to the practitioner in describing the compositions and methods of the disclosure and how to make and use them.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "fragrance sample" is taken to mean any individual material, e.g., a fragrance composition (which is synonymous with perfume ingredient and perfume material), which may contain one or more musk or fragrance accords. It is also understood that a "fragrance sample" can be a mixture of individual materials, such as, for example, multiple accords or a fully formulated fragrance. As used herein, the term "fragrance" may be used interchangeably with the term "perfume".

As used herein, the term "accord" refers to a formulation that contains one or more different musk compounds that create a specific smell, odor or scent, and that causes a specific physiological effect when used in proper effective amounts as necessary.

As used herein, the term "stressor" and "stress stimuli" are used interchangeably and refer to one of more event(s) which induces a stress response in a subject. The stressor can be chemical, biological, environmental, or another external stimulus that causes a stress reaction within a subject's body.

As used herein, the term "subject" refers to a human or a non-human subject. Non-limiting examples of non-human subjects include non-human primates, dogs, cats, mice, rats, guinea pigs, rabbits, pigs, fowl, horses, cows, goats, sheep, cetaceans, etc.

As used herein, the term "treat" or "treating" refers to intervention to alter (e.g., lower) the stress level of the subject, e.g., by administering a fragrance composition.

As used herein, the term "reduce" refers to alter negatively by at least about 5% including, but not limited to, alter negatively by about 5%, by about 10%, by about 25%, by about 30%, by about 50%, by about 75%, or by about 100%.

As used herein, the term "inhibit" or "prevent" refers to the ability of compound or composition, e.g., a fragrance composition, to stop, decrease, or reduce stress within a subject.

As used herein, the term "enantiomers" refers to a pair of stereoisomers that are non-superimposable mirror images of each other. A 1:1 mixture of a pair of enantiomers is a "racemic" mixture. The term is used to designate a racemic mixture where appropriate.

As used herein, the term "diastereoisomers" refers to stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro or levorotatory) which they rotate plane polarized light at the wavelength of the sodium D line. The compounds of the presently disclosed subject matter contain one or more asymmetric centers and may thus give rise to enantiomers, diastereomers, and other stereoisomeric forms that may be defined, in terms of absolute stereochemistry, as (R)- or (S)-. The presently disclosed subject matter is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "isomers" refers to different compounds that have the same molecular formula but differ in arrangement and configuration of the atoms. Also as used herein, the term "stereoisomer" refers to any of the various stereo isomeric configurations which may exist for a given compound of the presently disclosed subject matter and includes geometric isomers. It is understood that a substituent may be attached at a chiral center of a carbon atom. Therefore, the presently disclosed subject matter includes enantiomers, diastereomers or racemates of the compound. Also as used herein, the terms "constitutional isomers"

refers to different compounds which have the same numbers of, and types of, atoms but the atoms are connected differently.

2. Musk Compounds

The fragrance compositions of the presently disclosed subject matter comprise one or more musk compounds. Although historically musk has been associated with an odorous substance from a male musk deer gland, musk is now understood to encompass a broad variety of compounds with similar odor characteristics. Musk is a class of aromatic compounds structurally grouped for example into polycyclic musks, macrocyclic musks, nitro musks, and acyclic musks. Although structurally diverse, each musk compound gives an odor, and the various compounds can be used alone or in combination. Because of their pleasant odor character, musk compounds have been incorporated into various product applications. Surprisingly, despite these odor similarities, the subject disclosure explains that it has been unexpectedly discovered that within the classes of musk compounds, only certain compounds act on the autonomic nervous system or the hypothalamus-pituitary-adrenal (HPA) axis to effectively treat, reduce, inhibit or prevent stress responses.

Musk fragrance compounds can include, but are not limited to, 4-Cyclopentadecen-1-one, (4Z); 4-Cyclopentadecen-1-one; 9-Cycloheptadecen-1-one; 9-Cycloheptadecen-1-one, (9Z); Oxacycloheptadecan-Z-one; ω-Hexadecanolide; 1,4-Dioxacyclohexadecane-5,16-dione; Oxacyclohexadecen-Z-one; 15-Pentadec-(11/12)-enolide; 1,4-Dioxacycloheptadecane-5, 17-dione; 3-Methyl-cyclopentadecanone; Oxacycloheptadec-10-en-2-one; 3-Methyl-cyclopentadecenone; 7/8-Cyclohexadecen-1-one; 8-Cyclohexadecen-1-one; Cyclohexadecanone; 15-Pentadecanolide, Oxacyclohexadecan-2-one; 3-Methyl-(5E/Z)-cyclotetradecen-1-one; 1[2,3-Dihydro-1,1,2,6-tetramethyl-3-(1-methylethyl)-1H-inden-5-yl]-ethanone; 1-(2,3-Dihydro-1,1,2,3,3,6-hexamethyl-1H-inden-5-yl)ethanone; 1-(5,6,7,8-Tetrahydro-3,5,5,6,8,8-hexalmeth-2-naphthalenyl)-ethanone; 1-[6-(1,1-Dimethylethyl)-2,3-dihydro-1,1-dimethyl-1H-inden-4-yl]-ethanone; Cyclopenta[g]-2-benzopyrane, 1,3,4,6,7,8-hexahydro-4,6,6,7,8,8-hexamethyl-; 1-Propanol, 2-[1-(3,3 dimethylcyclohexyl)ethoxy]-2-methyl-,1-propanoate; 2,3-Dihydro-1,1,3,3,5-pentamethyl-4,6-dinitro-1H-indene; 1-(1,1-Dimethylethyl)-3,4,5-trimethyl-2,6-dinitrobenzene; 1-[4-(1,1-Dimethylethyl)-2,6-dimethylphenyl]-ethanone; 1-(1,1-Dimethylethyl)-3,5-dimethyl-2,4,6-trinitrobenzene; 1-[4-(1,1-Dimethylethyl)-2,6-dimethyl-3,5-dinitrophenyl]ethanone; and including constitutional isomers, enantiomers, stereoisomers and racemic mixtures of said compounds listed herein. Non-limiting examples of musk compounds are further described, for example, in www.thegoodscentscompany.com (last visited on Jun. 29, 2016).

Additional musk compounds include Applelide® (1-(3,3-dimethylcyclohexyl)ethyl propanedioic acid ethyl ester); Celestolide® (1-(6-tert-butyl-1,1-dimethyl-2,3-dihydroinden-4-yl)ethanone); Cosmone® ((5E)-3-methylcyclotetradec-5-en-1-one); Exaltolide (16-oxacyclohexadecan-1-one); Exaltone® (cyclopentadecan-1-one); Fixolide® (1-(3,5,5,6,8,8-hexamethyl-5,6,7,8-tetrahydronaphthalen-2-yl)ethanone); Globanone® ((8E)-cyclohexadec-8-en-1-one); Muscenone® ((5E)-3-methylcyclopentadec-5-en-1-one); Musk 15® (cyclopentadecanone); Musk Ambrette® (1-tert-butyl-2-methoxy-4-methyl-3,5-dinitrobenzene); Musk C-14® (2,5-dioxacyclohexadecane-1,6-dione); MUSK R-1® (1,7-dioxacycloheptadecan-8-one); Nirvanolide® (12-methyl-14-tetradec-9-enolide); Oxalide T® (1,8-dioxacycloheptadecan-9-one); Serenolide® (2-[1-(3,3-dimethylcyclohexyl)ethoxy]-2-methylpropyl cyclopropanecarboxylate); Sylkolide® ((3'E)-2-((3',5'-dimethylhex-3'-en-2'-yl)oxy)-2-methylpropyl cyclopropanecarboxylate); Velvione® ((5Z)-cyclohexadec-5-en-1-one); Versalide® (1-(3-ethyl-5,5,8,8-tetramethyl-6,7-dihydronaphthalen-2-yl)ethanone); Vulcanolide® (3,5,5,6,7,8,8-heptamethyl-5,6,7,8-tetrahydronaphthalene-2-carbaldehyde); and including constitutional isomers, enantiomers, stereoisomers and racemic mixtures of said compounds listed herein.

Additional musk compounds include rosamusk (1-(3,3-dimethylcyclohexyl)ethyl acetate), Habanolide® ((12E)-1-oxacyclohexadec-12-en-2-one), ambrettolide (17-oxacycloheptadec-6-en-1-one), Ambretone® (5-Cyclohexadecen-1-one), Musk T® (ethylene brassylate), Musk C14® (ethylene dodecanoate), Musk R1 (11-Oxahexadecan-16-olide), 1-oxacyclohexadec-12-en-2-one, Muscone, L-Muscone, 3-methyl-5-((1R)-2,2,3-trimethylcyclopentyl)pentan-2-one, phantolide (1-(1,1,2,3,3,6-hexamethyl-2H-inden-5-yl)ethanone), Hindinol® ((E)-2-methyl-4-(2,2,3-trimethyl-1-cyclopent-3-enyl)but-2-en-1-ol), traesolide (5-Acetyl-1,1,2,6-tetramethyl-3-isopropylindan), cashmeran (1,2,3,5,6,7-hexahydro-1,2,3,3-pentamethyl-4h-inden-4-one), tonalide (1-(3,5,5,6,8,8-hexamethyl-6,7-dihydronaphthalen-2-yl) ethanone), Helvetolide® ([2-[1-(3,3-dimethylcyclohexyl) ethoxy]-2-methylpropyl]propanoate), galaxolide (4,6,6,7,8,8-hexamethyl-1,3,4,6,7,8-hexahydro-cyclopenta[g]-isochromene), Romandolide® (acetic acid, (1-oxopropoxy)-1-(3,3-dimethylcyclohexyl) ethyl ester), Cetalox® (3a,6,6,9a-tetramethyl-2,4,5,5a,7,8,9,9b-octahydro-1H-benzo[e][1]benzofuran), and musk ketone; and including constitutional isomers, enantiomers, stereoisomers and racemic mixtures of said compounds listed herein.

In one embodiment, the musk compound is selected from the group consisting of rosamusk (1-(3,3-dimethylcyclohexyl)ethyl acetate), Habanolide® ((12E)-1-oxacyclohexadec-12-en-2-one), ambrettolide (17-oxacycloheptadec-6-en-1-one), L-Muscone, 3-methyl-5-((1R)-2,2,3-trimethylcyclopentyl)pentan-2-one, phantolide (1-(1,1,2,3,3,6-hexamethyl-2H-inden-5-yl)ethanone), Hindinol® ((E)-2-methyl-4-(2,2,3-trimethyl-1-cyclopent-3-enyl)but-2-en-1-ol), and combinations thereof.

In specific embodiments, the one or more musk compounds (taken alone or together) make up a musk or fragrance accord. In one embodiment, one musk compound makes up the musk accord. In another embodiment, two musk compounds make up the musk accord. In another embodiment, three musk compounds make up the musk accord. In yet another embodiment, four or more musk compounds make up the musk accord. These musk accords are then used in fragrance compositions as discussed in more detail below.

3. Fragrance Compositions

The musk or fragrance accord of the presently disclosed subject matter can be formulated into different fragrance compositions. As discussed above, each accord contains at least one musk compound.

In certain embodiments, the one or more musk or fragrance accords of the present disclosure are formulated in a fragrance composition in amounts of from about 0.001% to about 99% by weight of the total fragrance composition, or from about 0.01% to about 90% by weight, or from about 0.1% to about 80% by weight, or from about 1% to about 70% by weight, or from about 2% to about 60% by weight, or from about 5% to about 50% by weight, or from about 5% to about 40% by weight, or from about 5% to about 30% by weight, or from about 5% to about 20% by weight, or from about 5% to about 10% by weight of the total fragrance composition. In certain embodiments, the fragrance compositions of the present disclosure contain at least about 5%, at least about 10%, at least about 20%, or at least about 25% by weight of a musk or fragrance accord.

In certain embodiments, the fragrance compositions of the present disclosure contain at least about 98.5% by weight of a musk or fragrance accord. In one embodiment, the fragrance composition contains 100% by weight of a musk or fragrance accord.

A fragrance composition can include, but is not limited to, one or more musk accords, and one or more additional fragrance accords or compounds. In certain embodiments, the additional fragrance accords or compounds can but are not limited to, one or more musk compound(s), one or more a woody compound(s), one or more floral compound(s) and/or one or more amber compound(s), or combinations thereof.

Additional fragrance compounds, including but not limited to one or more of the compounds disclosed herein, can also be included in the compositions so long as the addition does not change the ability of the composition to treat, reduce, inhibit or prevent stress responses.

In certain embodiments, the additional fragrance compounds are formulated in a composition in an amount of from about 0.001% to about 99% by weight, or from about 0.01% to about 90% by weight, or from about 0.1% to about 80% by weight, or from about 1% to about 70% by weight, or from about 2% to about 60% by weight, or from about 5% to about 50% by weight, or from about 10% to about 40% by weight, or from about 15% to about 30% by weight, or from about 20% to about 25% by weight.

In certain embodiments, the fragrance compositions of the present disclosure include one or more fragrance accords. In certain embodiments, each fragrance accord can comprise two or more compounds. In certain embodiments, the additional accord can comprise at least one musk compound.

4. Use of Compositions in Consumer Products

In certain embodiments, the fragrance compositions of the present disclosure are formulated as part of a consumer product.

The compositions of the presently disclosed subject matter relate to fragrance formulations, and/or a flavor formulations, in which the compositions are blended as a calming or sedative effect-providing fragrance and/or flavor modifier, and the fragrance and/or flavor formulation can be used in, for example, perfumes, colognes, shampoos, rinses, skin cares, body shampoos, body rinses, body powders, air fresheners, deodorants, baths, foods, snacks, beverages, and the like, if necessary in combination with auxiliary materials.

In certain embodiments, the consumer products of the present disclosure can be, but are not limited to, air care products (e.g., candles, aerosols, air fresheners, liquid electric air fresheners, fragrance diffusers, gel air fresheners, plug-in air fresheners, etc.); baby care products (e.g., consumer products relating to disposable absorbent and/or non-absorbent articles, including adult incontinence garments, bibs, diapers, training pants, infant and toddler care wipes; and personal care products including hand soaps, shampoos, lotions, and clothing); fabric and home care products (e.g., consumer products for fabric conditioning (including soft- ening), laundry detergency, laundry and rinse additive and/or care, dryer sheets, perfume beads, air care, car care, dishwashing, hard surface cleaning and/or treatment, and other cleaning for consumer and or institutional use, etc.); personal care products (e.g., lotions, creams, body washes, hand soaps, shampoos, conditioners, soaps, etc.); family care products (e.g., wet or dry bath tissue, facial tissue, disposable handkerchiefs, disposable towels, and/or wipes, towels, toilet paper, tissue paper, wet towels, etc.); feminine care products (e.g., catamenial pads, incontinence pads, interlabial pads, panty liners, pessaries, sanitary napkins, tampons and tampon applicators, and/or wipes, etc.); sexual health care products (e.g., products relating to sexual aids or sexual health, including lubricants and condoms, etc.); pet care products (e.g., pet malodor cat litter, pet deodorizers, pet health and nutrition including pet foods, treats, other orally deliverable products, grooming aids, products for treating pet hair/fur including shampooing, styling, conditioning; deodorants and antiperspirants; products for cleansing or treating pet skin, including soaps, creams, lotions, and other topically applied products; training aids, toys and diagnostics techniques); fine fragrance (including hydro alcoholic solutions of perfume oil, such as parfum/extrait de parfum, eau de parfum/millesime/parfum de toilette, eau de toilette, eau de cologne, body splash, after shave, body mists, including baby colognes); auto care products (e.g., cleaners, air fresheners, wipes, soaps, etc.); cosmetics (e.g., skin cream, cleansing cream, night cream, hand cream, lotion, after-shave lotion, body lotion, foundation, lip stick, lip cream, nail polish, nail polish remover, talcum powder, anti-wrinkle and/or anti-aging cosmetics, sun protection products, massage oil, etc.); beauty care (e.g., products for treating human hair including shampooing, styling, conditioning; deodorants and antiperspirants; products for personal cleansing; products for treating human skin, including application of creams, lotions, and other topically applied products; products for shaving, rinse, rinse in shampoo; hair styling agents such as pomade, hair tonic, hair gel, hair cream and hair mousse; hair growing agents; hair coloring agents, etc.); and bath agents (e.g., powder bath additives, solid foaming bath additives, bath oils, bubble bath aroma generators, bath salts, etc.); hair removal products (e.g., products for hair removal including depilatory creams, sugar pastes or gels, waxes); writing products (e.g., pens, crayons, paints, pencils, paper, origami, seals, etc.); products for play (e.g., balls, beanbags, cards, tops, dolls, building blocks, etc.); flavored products (e.g., confections, beverages, snacks, prepared meals, OTC medications, gum, etc.); pharmaceuticals (e.g., plasters, ointments, suppositories, tablets, liquid medicines, capsules, granules, pharmacologically active molecular and/or biological entities; their use in the treatment and/or prevention of diseases and/or alleviation of symptoms in humans and/or animals, and formulations, regimens, kits and/or routes of delivering such entities to subjects in need of treatment and/or prevention and/or alleviation, etc.); health care products (e.g., oral health care products, including any composition for use with any soft and/or hard tissue of the oral cavity or conditions associated therewith (e.g., anti-cavities compositions, anti-plaque chewing gum compositions, breath compositions, dentrifices, denture compositions, lozenges, rinses, and tooth whitening compositions), cleaning devices, floss and flossing devices and toothbrushes; over-the-counter health care including cough and cold remedies and treatments for other respiratory conditions, pain relievers whether topical, oral, or otherwise, gastrointestinal remedies including any composition suitable for the alleviation of gastrointestinal conditions such as heartburn, upset stomach, diarrhea, and irritable bowel syndrome, and nutrient supplementation such as calcium or fiber supplementation, etc.); and foods and drinks or beverage (e.g., confectioneries consisting of gum, candy, snack such as potato crisps, baked sweets such as cookie and biscuit; drinks including refreshing drinks such as flavored tea, herb tea, juice, soda and powdered drink, fancy drinks such as tea and coffee, and milk drinks; frozen desserts such as ice cream, sherbet, mousse and frozen yogurt; desserts such as custard pudding, jelly, bavarois, yogurt and cream; cooked foods such as soup, curry and stew; seasonings such as condensed soup for noodles, dressing and mayonnaise; bakery products such as bread and donuts; daily products such as butter cream and margarine; fish paste products; etc.).

In certain embodiments, the disclosed subject matter provides for use of the compositions described herein in a consumer product as described herein.

In certain embodiments, the fragrance compositions are formulated as part of a product to reduce stress.

In certain embodiments, the fragrance compositions are formulated as part of a product which is relaxing or sedating.

In certain embodiments, the subject disclosure relates to methods of incorporating stress-reducing or inhibiting effects into a consumer product. In certain embodiments, methods include a) providing at least one consumer product, and b) combining the consumer product with a fragrance composition comprising at least one, two, three or more musk compounds. For example, in one non-limiting embodiment a consumer product may be combined with a composition comprising 1-(3,3-dimethylcyclohexyl)ethyl acetate, ((12E)-1-oxacyclohexadec-12-en-2-one), 17-oxacycloheptadec-6-en-1-one, L-Muscone, 3-methyl-5-((1R)-2,2,3-trimethylcyclopentyl)pentan-2-one, 1-(1,1,2,3,3,6-hexamethyl-2H-inden-5-yl)ethanone, ((E)-2-methyl-4-(2,2,3-trimethyl-1-cyclopent-3-enyl)but-2-en-1-ol).

In one embodiment, at least a fragrance composition comprising one, two, three or more musk compounds can be added to a consumer product, such as an air care product, to reduce the level of stress in a subject using the product as compared to the level of stress of a subject using a consumer product which does not comprise the subject composition. For example, a composition comprising two musk compounds may be added to a consumer product, such as air freshener, which is utilized by a subject before exposure to a stressor and effectively reduces the subject's stress. In other embodiments, the product may be utilized by a subject during or after exposure to a stressor, which effectively reduces the subject's stress.

The concentration and/or amount of the fragrance composition admixed with the consumer product to reduce or inhibit stress in a consumer can change based on a number of variables, for example, the specific consumer product, the physical form of the consumer product (e.g., liquid, gas, or solid) and what fragrance compounds are already present in the consumer product and the concentrations and/or amounts thereof.

A broad range of concentrations and/or amounts of the fragrance composition can be employed to reduce or inhibit the level of stress in a consumer. In certain embodiments of the present disclosure, the fragrance composition is admixed with a consumer product and the composition is present in the consumer product in an amount from about 1 to about 9000 ppm, or from about 5 to about 7500 ppm, or from about 10 to about 5000 ppm, or from about 50 to about 2500 ppm, or from about 100 to 1000 ppm, or from about 250 to 500 ppm, and any value in between.

In certain embodiments of the present disclosure, the fragrance composition is admixed with a consumer product wherein the composition is present in an amount from about 0.0001 to about 90% weight/weight (w/w), or from about 0.001 to about 75% w/w, or from about 1 to about 50% w/w, or from about 5 to about 25% w/w, or from about 10 to about 15% w/w, and values in between.

In certain embodiments, the fragrance composition admixed with the consumer product comprises the musk compound 1-(3,3-dimethylcyclohexyl)ethyl acetate, ((12E)-1-oxacyclohexadec-12-en-2-one), 17-oxacycloheptadec-6-en-1-one, L-Muscone, 3-methyl-5-((1R)-2,2,3-trimethylcyclopentyl)pentan-2-one, 1-(1,1,2,3,3,6-hexamethyl-2H-inden-5-yl)ethanone, ((E)-2-methyl-4-(2,2,3-trimethyl-1-cyclopent-3-enyl)but-2-en-1-ol), or a combination thereof of at least two, or at least three musk compounds.

In certain embodiments, the fragrance composition additionally includes one or more bases, solvents and combinations thereof.

In certain embodiments, bases can include, but are not limited to, essential oils, lactones, aldehydes, alcohols, ketones, nitriles, esters, amides, oximes, and other fragrant compounds and perfuming co-ingredients.

In certain embodiments, the solvents can include, but are not limited to, diproplyene glycol, propylene glycol, diethphthalate (DEP), diisononyl phthalate (DINP), benzyl benzoate, benzyl alcohol, iso propyl myristate (IPM), isopropyl palmitate (IPP/Deltyl Prime), butyl stearate, dioctyl adipate, triethyl citrate, methyl hydrogenated rosinate (CAS No. 8050-15-5), terpenes (e.g., Glidsol 100), paraffinic napthenic solvent (e.g., LPA-170 Solvent), isoalkanes (e.g., Soltrol 170 Isoparaffin), isoparaffins, isooctadecanol, (e.g., Tego Alkanol 66), phenoxyethanol, diethylene glycol monoethyl ether (Carbitol low gravity), glycol ether (Methyl Carbitol), Dipropylene Glycol Methyl Ether (e.g., Dowanol DPM), Dipropylene Glycol Methyl Ether Acetate (e.g., Dowanol DPMA), Propylene glycol methyl ether (e.g., Dowanol PM Glycol Ether), Tripropylene Glycol Methyl Ether, Diisoheptyl Phthalate (e.g., Jayflex® 77 available from Exxon), deionized or distilled water, specially denatured ethyl alcohol (e.g., SDA 40B), Dimethyl Adipate/Dimethyl Glutarate (e.g., DBE®-LVP Esters available from FLEXISOLV®), Racemic mixture (+/−)-2,2-dimethyl-4-hydroxymethyl-1,3-dioxolane (e.g., Augo Clean Multi Solvent), Alcohol 40B Anhydrous 200 Proof, alcohol SDA 40B 190 Proof, Triacetin, 3-Methoxy-3-methyl-1-butanol (Solfit), Benzyl Laurate, Tripropylene Glycol Methyl Ether (e.g., Dowanol TPM), Dipropylene glycol n-butyl ether (e.g., Dowanol DPNB), Dimethyl siloxane, trimethylsiloxy-terminated (e.g., Dowanol Corning 200 Fluid), Caprylic/Capric Triglycerides (e.g., Neobee M-5), propylene glycol and glyceryl oleate (e.g., Arlacel 186), Uniceth-IC20L (e.g., Arlasolve 200 L), propanediol, 1, 3, Butyl Cellosolve, Hexylene glycol, Glycerine, N Methyl Stearate, Isopropyl alcohol, 2-Methyl-1,3-propanediol (e.g., MP Diol Glycol), Diethyl Citrate, Triethyl Acetyl Citrate, Isopentyldiacetate (IPD-AC, Dimethyl 2-methylpentanedioate (e.g., Rhodiasolv Iris), medium chain triglicyrides (MTC), terpene hydrocarbons (e.g., Dipentene 5100, DL-limonene (e.g., Dipentene 122), 3,5,5-trimethylhexyl acetate, Diethyl Malonate, Limonene (e.g., Unitene D), cyclohexyl acetate, para-tertiary-butyl (e.g., Vertenex), Ethyl Acetate, Diethyl Succinate.

In certain embodiments, the presently disclosed subject matter includes:

a) A consumer product comprising a sufficient amount of at least one musk compound selected from the group consisting of 1-(3,3-dimethylcyclohexyl)ethyl acetate, ((12E)-1-oxacyclohexadec-12-en-2-one), 17-oxacycloheptadec-6-en-1-one, L-Muscone, 3-methyl-5-((1R)-2,2,3-trimethylcyclopentyl)pentan-2-one, 1-(1,1,2,3,3,6-hexamethyl-2H-inden-5-yl)ethanone, ((E)-2-methyl-4-(2,2,3-trimethyl-1-cyclopent-3-enyl)but-2-en-1-ol), and combinations thereof to provide a concentration of said at least one musk of at least 7 nanograms per cubic foot of air, preferably from 7.4 nanograms per cubic foot of air to 28 nanograms per cubic foot of air, more preferably 7.4 nanograms per cubic foot of air to about 27.7 nanograms per cubic foot of air, said consumer product being a fabric and home care product, baby care product, beauty care product, family care product and/or a feminine care product is disclosed.

b) The consumer product of Paragraph a), wherein the at least one musk compound is selected from the group consisting of ((12E)-1-oxacyclohexadec-12-en-2-one), and combinations thereof is disclosed.

c) The consumer product according to Paragraphs a) or b), said consumer product comprising, in addition to said at least one musk compound, one or more fragrance raw materials is disclosed.

d) The consumer product according to any of Paragraphs a) through c) wherein said at least one musk compound is provided, at least in part, by a fragrance delivery system, preferably said fragrance delivery system is selected from the group consisting of a Polymer Assisted Delivery (PAD) system, Molecule-Assisted Delivery (MAD) system, Cyclodextrin (CD) system, Starch Encapsulated Accord (SEA) system, Zeolite & Inorganic Carrier (ZIC) system, more preferably, said Polymer Assisted Delivery (PAD) system comprises a Polymer Assisted Delivery (PAD) Reservoir system, preferably said Polymer Assisted Delivery (PAD) Reservoir system comprises a fragrance delivery particle that comprises a shell material and a core material, said shell material encapsulating said core material, said core material comprising said at least one musk compound and said shell comprising a material selected from the group consisting of polymethacrylates; polyethylenes; polyamides; polystyrenes; polyisoprenes; polycarbonates; polyesters; polyacrylates; aminoplasts, preferably said aminoplast comprises a polyureas, polyurethane, and/or polyureaurethane, preferably said polyurea comprises polyoxymethyleneurea and/or melamine formaldehyde, more preferably said polyurea comprises melamine formaldehyde and/or cross linked melamine formaldehyde; polyolefins; polysaccharides, alginate and/or chitosan; gelatin; shellac; epoxy resins; vinyl polymers; water insoluble inorganics; silicone; and mixtures thereof, preferably said shell is coated by a water-soluble cationic polymer selected from the group that consists of polysaccharides, cationically modified starch and cationically modified guar, polysiloxanes, dimethyldiallylammonium polyhalogenides, copolymers of dimethyldiallylammonium polychloride and vinyl pyrrolidone, acrylamides, imidazoles, imidazolinium halogenides and imidazolium halogenides and polyvinyl amine and its copolymers with N-vinyl formamide is disclosed.

e) The consumer product according to any of Paragraphs a) through d), said consumer product comprising, based on total consumer product weight:
(i) from 0.1% to 99%, preferably from 1% to 80%, more preferably from 5% to 55%, most preferably from 10% to 50% of a solvent, preferably said solvent is selected from cyclopentasiloxane, ethanol, water, propylene glycol, dipropylene glycol, and mixtures thereof; and (ii) from 0% to 30%, preferably from 0% to 20%, more preferably from 0.1% to 4%, most preferably from 0.1% to 4% of a material selected from the group consisting of a structurant, a residue masker, an antimicrobial, and mixtures thereof, is disclosed.

f) A consumer product according to any of Paragraphs a) through e), said consumer product comprising from 1% to 25% of an antiperspirant active selected from the group consisting of astringent metallic salts, preferably inorganic and organic salts of aluminum, zirconium and zinc, as well as mixtures thereof, more preferably aluminum halides, aluminum chlorohydrate, aluminum hydroxyhalides, zirconyl oxyhalides, zirconyl hydroxyhalides, and mixtures thereof is disclosed.

g) A consumer product according to any of Paragraphs a) through c), wherein said consumer product is a device, preferably said device is selected from the group consisting of energized air fresheners and non energized air fresheners, more preferably said device is selected from the group consisting of:
(i) wick air fresheners;
(ii) reservoir air fresheners;
(iii) porous membrane air fresheners;
(iv) power assisted delivery air fresheners, preferably power assisted delivery air fresheners selected from the group consisting of thermal drop-on-demand air fresheners, piezo air fresheners, heater air fresheners, fan air fresheners, or microfluidic devices air fresheners; and
(v) spray devices
is disclosed.

h) A consumer product according to any of Paragraphs a) through c), comprising an ingredient selected from the group consisting of builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, hueing dyes, fragrances, fragrance delivery systems, structure elasticizing agents, carriers, structurants, hydrotropes, processing aids, solvents in addition to said solubilizing agent, a fabric softener active selected from the group consisting of a silicone polymer, a polysaccharide, a clay, a fatty ester, a dispersible polyolefin, a polymer latex and mixtures thereof, pigments, and mixtures thereof i) A consumer product according to any of Paragraphs a) through d), said consumer product comprising, based on total consumer product weight:
(i) from 0.1% to 99%, preferably from 1% to 80%, more preferably from 5% to 70%, most preferably from 10% to 50% of a solvent, preferably said solvent is selected from, water, glycerin, and mixtures thereof; and
(ii) from 0% to 50%, preferably from 0% to 40%, more preferably from 0.1% to 30%, most preferably from 0.1% to 15% of a material selected from the group consisting of a structurant, a humectant, a surfactant, an antimicrobial, and mixtures thereof
is disclosed.

j) A consumer product according to Paragraph i), said consumer product comprising, based on consumer product weight, from 3% to 30% of a surfactant, and, optionally, a miscellar phase and/or lamellar phase is disclosed.

k) A consumer product according to Paragraph i), said consumer product comprising, based on consumer product weight, from 0.1% to 50% of a material selected from structurants, humectants, fatty acids, inorganic salts, antimicrobial agents, antimicrobial actives and mixtures thereof is disclosed.

l) A consumer product according to any of Paragraphs i)-k), said consumer product comprising, an ingredient selected from the group consisting of clay mineral powders, pearl pigments, organic powders, emulsifiers, distributing agents, pharmaceutical active, topical active, preservatives, surfactants and mixtures thereof is disclosed.

m) A method of reducing or inhibiting a stress response in a subject in need thereof comprising: using the consumer product of any one of Paragraphs a) through l) in an amount effective to reduce or inhibit a response to stress stimuli is disclosed.

n) The method of Paragraph m), wherein the composition is used before exposure to the stress stimuli is disclosed.

5. Reduction or Inhibition of Stress

In certain embodiments, the compositions of the presently disclosed subject matter are administered in an amount effective to reduce or inhibit stress in a subject.

5.1 Methods of Composition Administration

In certain embodiments of the present disclosure, the composition comprising one or more musk compounds is administered to a subject prior to, during, or after exposure to a stressor to reduce or inhibit the subject's stress level.

In one non-limiting embodiment, the composition is administered to a subject through gaseous or volatile form. In these embodiments, the composition is administered intranasally or by inhalation. In certain embodiments, the subject inhales the composition directly or indirectly.

In further embodiments, the composition is administered via a consumer product. In one non-limiting example, the composition is admixed with a consumer product. The subject then uses the consumer product comprising the composition. Depending on the use of the consumer product, the subject is exposed to the fragrance composition.

In a specific embodiment, the composition is released into the area surrounding the subject and the subject then inhales the composition. In one non-limiting example, the composition is released into the air by a consumer product, such as an air freshener.

In certain embodiments of the present disclosure, the amount of the composition released from the consumer product is less than the total concentration of the composition admixed with the consumer product. In certain embodiments, the amount of the composition released by the consumer product, and therefore available for administration to the subject, is between about 1 and 100% of the amount of composition admixed with the consumer product. In further embodiments, the amount of composition released is between about 5 and 90%, between about 10 and 80%, between about 20 and 70%, between about 30 and 60%, and between about 40 and 50% of the amount of composition admixed with the consumer product.

5.2 Methods of Measuring Stress Relief

In certain embodiments, the compositions of the presently disclosed subject matter are administered in an amount effective to reduce or inhibit stress in a subject as determined by measuring the levels of specific hormones in a subject. In certain embodiments, the composition is incorporated into a consumer product, as discussed above, which is utilized by a subject before, during, or after exposure to a stressor.

5.2.1 Biomarkers

In certain embodiments, the compositions of the presently disclosed subject matter are administered to a subject, a stressor is applied, and specific biomarkers are measured to determine the level of stress reduction or inhibition.

In specific embodiments, the compositions of the presently disclosed subject matter are effective at reducing or inhibiting stress if a change in cortisol, or salivary amylase, or both are detected.

5.2.1.1 Cortisol

Cortisol is released by the body as part of a longer term response to stress, resulting from the activation of the hypothalamus-pituitary-adrenal (HPA) axis. A change in cortisol levels therefore indicates an subject's reaction, or lack therefor, to a stressor.

Accordingly, in certain embodiments of the subject disclosure, salivary cortisol levels are measured as biomarkers to determine a subject's reaction, or lack thereof, to a stressor. A reduction in, or maintenance of, the level of biomarker indicates that the composition reduced or inhibited stress in a subject. In certain embodiments, the subject's level of salivary cortisol is measure before and after the application of a stressor. In certain embodiments the salivary cortisol level is measured, the composition is administered, the stressor is applied and then the salivary cortisol level is measured again. The percent change in the salivary cortisol level can then be calculated.

In certain embodiments, the composition is administered to a subject in an amount effective to reduce or maintain the level of salivary cortisol in the subject when the subject is exposed to a stressor as compared to the level of salivary cortisol in the subject before exposure to the stressor. In certain embodiments, the reduction in the level of salivary cortisol is between about 1 and about 100%, or between about 2 and about 75%, or between about 5 and about 50%, or between about 10 and about 45%, or between about 15 and about 40%, or between about 20 and about 35%, or between about 25 and about 30%. In certain embodiments, the reduction in the level of salivary cortisol is between about 1 and about 50%, or between about 1 and about 40%, or between about 1 and about 30%, or between about 1 and about 20%, or between about 1 and about 10%, or between about 1 and about 5%.

5.2.1.2 Alpha-Amylase

Salivary alpha-amylase is a digestive enzyme produced in and released from the saliva glands. Levels of salivary alpha-amylase increase in response to psychological and physical stress through interactions with the autonomic nervous system. Accordingly, in certain embodiments of the subject disclosure, salivary alpha-amylase levels are measured to determine an subject's reaction, or lack thereof, to a stressor. A reduction in, or maintenance of, the level of salivary alpha-amylase indicates that the composition reduced or inhibited stress in a subject. In certain embodiments, the subject's level of salivary alpha-amylase is measured before and after the application of a stressor. In certain embodiments the salivary alpha-amylase level is measured, the composition is administered, the stressor is applied and then the salivary alpha-amylase level is measured again. The percent change in the salivary alpha-amylase level can then be calculated.

In certain embodiments, the composition is administered to a subject in an amount effective to reduce the level of salivary alpha-amylase in the subject when the subject is exposed to a stressor as compared to the level of salivary alpha-amylase in the subject before, during, or after exposure to the stressor.

In certain embodiments, the reduction in the level of salivary alpha-amylase is between about 15 and about 200%, or between about 20 and about 180%, or between about 25 and about 160%, or between about 30 and about 140%, or between about 35 and about 120%, or between about 40 and about 115%, or between about 45 and about 110%, or between about 50 and about 105%, or between about 50 and about 100%, or between about 55 and about 95%, or between about 60 and about 90%, or between about 65 and about 85%, or between about 70 and about 80%.

In certain embodiments, the reduction in the level of salivary alpha-amylase is at least about 2%, about 5%, about 7.5%, about 10%, about 15%, or about 20%.

In certain embodiments, the reduction in the level of salivary alpha-amylase is between about 2% and about 100%, or between about 2% and about 75%, or between about 2% and about 50%, or between about 2% and about 40%, or between about 2% and about 30%, or between about 2% and about 20%, or between about 5% and about 20%.

6. Fragrance Delivery Systems

The benefits of the musks disclosed herein may be further enhanced by employing a delivery system to apply such musks. Non-limiting examples of suitable delivery systems, methods of making delivery systems and the uses of such delivery systems are disclosed in U.S. Patent publication no. 2007/0275866 A1. Such delivery systems include the following.

Polymer Assisted Delivery (PAD): This fragrance delivery technology uses polymeric materials to deliver fragrance materials. Classical coacervation, water soluble or partly soluble to insoluble charged or neutral polymers, liquid crystals, hot melts, hydrogels, fragranced plastics, microcapsules, nano- and micro-latexes, polymeric film formers, and polymeric absorbents, polymeric adsorbents, etc. are some examples. PAD includes but is not limited to:

Matrix Systems: The fragrance is dissolved or dispersed in a polymer matrix or particle. Fragrances, for example, may be 1) dispersed into the polymer prior to formulating into the product or 2) added separately from the polymer during or after formulation of the product. Diffusion of fragrance from the polymer is a common trigger that allows or increases the rate of fragrance release from a polymeric matrix system that is deposited or applied to the desired surface (situs), although many other triggers are known that may control fragrance release. Absorption and/or adsorption into or onto polymeric particles, films, solutions, and the like are aspects of this technology. Nano- or micro-particles composed of organic materials (e.g., latexes) are examples. Suitable particles include a wide range of materials including, but not limited to polyacetal, polyacrylate, polyacrylic, polyacrylonitrile, polyamide, polyaryletherketone, polybutadiene, polybutylene, polybutylene terephthalate, polychloroprene, polyethylene, polyethylene terephthalate, polycyclohexylene dimethylene terephthalate, polycarbonate, polychloroprene, polyhydroxyalkanoate, polyketone, polyester, polyetherimide, polyethersulfone, polyethylenechlorinates, polyimide, polyisoprene, polylactic acid, polymethylpentene, polyphenylene oxide, polyphenylene sulfide, polyphthalamide, polypropylene, polystyrene, polysulfone, polyvinyl acetate, polyvinyl chloride, as well as polymers or copolymers based on acrylonitrile-butadiene, cellulose acetate, ethylene-vinyl acetate, ethylene vinyl alcohol, styrene-butadiene, vinyl acetate-ethylene, and mixtures thereof.

"Standard" systems refer to those that are "pre-loaded" with the intent of keeping the pre-loaded fragrance associated with the polymer until the moment or moments of fragrance release. Such polymers may also suppress the neat product odor and provide a bloom and/or longevity benefit depending on the rate of fragrance release. One challenge with such systems is to achieve the ideal balance between 1) in-product stability (keeping fragrance inside carrier until you need it) and 2) timely release (during use or from dry situs). Achieving such stability is particularly important during in-product storage and product aging. This challenge is particularly apparent for aqueous-based, surfactant-containing products, such as heavy duty liquid laundry detergents. Many "Standard" matrix systems available effectively become "Equilibrium" systems when formulated into aqueous-based products. One may select an "Equilibrium" system or a Reservoir system, which has acceptable in-product diffusion stability and available triggers for release (e.g., friction). "Equilibrium" systems are those in which the fragrance and polymer may be added separately to the product, and the equilibrium interaction between fragrance and polymer leads to a benefit at one or more consumer touch points (versus a free fragrance control that has no polymer-assisted delivery technology). The polymer may also be pre-loaded with fragrance; however, part or all of the fragrance may diffuse during in-product storage reaching an equilibrium that includes having desired perfume raw materials (PRMs) associated with the polymer. The polymer then carries the fragrance to the surface, and releases it typically via fragrance diffusion. The use of such equilibrium system polymers has the potential to decrease the odor intensity of the neat product (usually more so in the case of pre-loaded standard systems). Deposition of such polymers may serve to "flatten" the release profile and provide increased longevity. As indicated above, such longevity would be achieved by suppressing the initial intensity and may enable the formulator to use more high impact or low odor detection threshold (ODT) or low Kovats Index (KI) PRMs to achieve FMOT benefits without initial intensity that is too strong or distorted. It is important that fragrance release occurs within the time frame of the application to impact the desired consumer touch point or touch points. Matrix systems also include hot melt adhesives and fragrance plastics. In addition, hydrophobically modified polysaccharides may be formulated into the fragranced product to increase fragrance deposition and/or modify fragrance release. All such matrix systems, including for example polysaccharides and nano-latexes may be combined with other PDTs, including other PAD systems such as PAD reservoir systems in the form of a perfume microcapsule (PMC).

Silicones are also examples of polymers that may be used as PDT, and can provide fragrance benefits in a manner similar to the polymer-assisted delivery "matrix system". Such a PDT is referred to as silicone-assisted delivery (SAD). One may pre-load silicones with fragrance, or use them as an equilibrium system as described for PAD. Examples of silicones include polydimethylsiloxane and polyalkyldimethylsiloxanes. Other examples include those with amine functionality, which may be used to provide benefits associated with amine-assisted delivery (AAD) and/or polymer-assisted delivery (PAD) and/or amine-reaction products (ARP).

Reservoir Systems: Reservoir systems are also known as a core-shell type technology, or one in which the fragrance is surrounded by a fragrance release controlling membrane, which may serve as a protective shell. The material inside the microcapsule is referred to as the core, internal phase, or fill, whereas the wall is sometimes called a shell, coating, or membrane. Microparticles or pressure sensitive capsules or microcapsules are examples of this technology. Microcapsules of the current invention are formed by a variety of procedures that include, but are not limited to, coating, extrusion, spray-drying, interfacial, in-situ and matrix polymerization. The possible shell materials vary widely in their stability toward water. Among the most stable are polyoxymethyleneurea (PMU)-based materials, which may hold certain PRMs for even long periods of time in aqueous solution (or product). Such systems include but are not limited to urea-formaldehyde and/or melamine-formaldehyde. Gelatin-based microcapsules may be prepared so that they dissolve quickly or slowly in water, depending for example on the degree of cross-linking. Many other capsule wall materials are available and vary in the degree of fragrance diffusion stability observed. Without wishing to be bound by theory, the rate of release of fragrance from a capsule, for example, once deposited on a surface is typically in reverse order of in-product fragrance diffusion stability. As such, urea-formaldehyde and melamine-formaldehyde microcapsules for example, typically require a release mechanism other than, or in addition to, diffusion for release, such as mechanical force (e.g., friction, pressure, shear stress) that serves to break the capsule and increase the rate of perfume (fragrance) release. Other triggers include melting, dissolution, hydrolysis or other chemical reaction, electromagnetic radiation, and the like. The use of pre-loaded microcapsules requires the proper ratio of in-product stability and in-use and/or on-surface (on-situs) release, as well as proper selection of PRMs. Microcapsules that are based on urea-formaldehyde and/or melamine-formaldehyde are relatively stable, especially in near neutral aqueous-based solutions. These materials may require a friction trigger which may not be applicable to all product applications. Other microcapsule materials (e.g., gelatin) may be unstable in aqueous-based products and may even provide reduced benefit (versus free perfume control) when in-product aged. Scratch and sniff technologies are yet another example of PAD.

Molecule-Assisted Delivery (MAD): Non-polymer materials or molecules may also serve to improve the delivery of fragrance. Without wishing to be bound by theory, fragrance may non-covalently interact with organic materials, resulting in altered deposition and/or release. Non-limiting examples of such organic materials include but are not limited to hydrophobic materials such as organic oils, waxes, mineral oils, petrolatum, fatty acids or esters, sugars, surfactants, liposomes and even other fragrance raw material (perfume oils), as well as natural oils, including body and/or other soils. Perfume fixatives are yet another example. In one aspect, non-polymeric materials or molecules have a C Log P greater than about 2.

Cyclodextrin (CD): This technology approach uses a cyclic oligosaccharide or cyclodextrin to improve the delivery of fragrance. Typically a fragrance and cyclodextrin (CD) complex is formed. Such complexes may be pre-formed, formed in-situ, or formed on or in the situs. Without wishing to be bound by theory, loss of water may serve to shift the equilibrium toward the CD-Fragrance complex, especially if other adjunct ingredients (e.g., surfactant) are not present at high concentration to compete with the fragrance for the cyclodextrin cavity. A bloom benefit may be achieved if water exposure or an increase in moisture content occurs at a later time point. In addition, cyclodextrin allows the fragrance formulator increased flexibility in selection of PRMs. Cyclodextrin may be pre-loaded with fragrance or added separately from fragrance to obtain the desired fragrance stability, deposition or release benefit.

Starch Encapsulated Accord (SEA): The use of a starch encapsulated accord (SEA) technology allows one to modify the properties of the fragrance, for example, by converting a liquid fragrance into a solid by adding ingredients such as starch. The benefit includes increased fragrance retention during product storage, especially under non-aqueous conditions. Upon exposure to moisture, a fragrance bloom may be triggered. Benefits at other moments of truth may also be achieved because the starch allows the product formulator to select PRMs or PRM concentrations that normally cannot be used without the presence of SEA. Another technology example includes the use of other organic and inorganic materials, such as silica to convert fragrance from liquid to solid.

Zeolite & Inorganic Carrier (ZIC): This technology relates to the use of porous zeolites or other inorganic materials to deliver fragrances. Perfume-loaded zeolite may be used with or without adjunct ingredients used for example to coat the perfume-loaded zeolite (PLZ) to change its perfume release properties during product storage or during use or from the dry situs. Silica is another form of ZIC. Another example of a suitable inorganic carrier includes inorganic tubules, where the perfume or other active material is contained within the lumen of the nano- or micro-tubules. Preferably, the perfume-loaded inorganic tubule (or Perfume-Loaded Tubule or PLT) is a mineral nano- or micro-tubule, such as halloysite or mixtures of halloysite with other inorganic materials, including other clays. The PLT technology may also comprise additional ingredients on the inside and/or outside of the tubule for the purpose of improving in-product diffusion stability, deposition on the desired situs or for controlling the release rate of the loaded fragrance. Monomeric and/or polymeric materials, including starch encapsulation, may be used to coat, plug, cap, or otherwise encapsulate the PLT.

In one aspect, a fragrance delivery system selected from the group consisting of a Polymer Assisted Delivery (PAD) system, Molecule-Assisted Delivery (MAD) system, Cyclodextrin (CD) system, Starch Encapsulated Accord (SEA) system, Zeolite & Inorganic Carrier (ZIC) system, wherein said fragrance delivery system may comprise a fragrance disclosed in this specification, for example a fragrance selected from the fragrances disclosed in the fragrance section of this specification, is disclosed.

In one aspect, a Polymer Assisted Delivery (PAD) system wherein said Polymer Assisted Delivery (PAD) system may comprise a Polymer Assisted Delivery (PAD) Reservoir system that may comprise a fragrance disclosed in this specification, for example a fragrance selected from the fragrances disclosed in the fragrance section of this specification, is disclosed.

In one aspect of, said Polymer Assisted Delivery (PAD) Reservoir system said Polymer Assisted Delivery (PAD) Reservoir system may comprise a fragrance delivery particle that may comprise a shell material and a core material, said shell material encapsulating said core material, said core material may comprise a fragrance disclosed in this specification, for example a fragrance selected from the fragrances disclosed in the fragrance section of this specification, and said shell comprising a material selected from the group consisting of polyethylenes; polyamides; polystyrenes; polyisoprenes; polycarbonates; polyesters; polyacrylates; aminoplasts, in one aspect said aminoplast comprises a polyurea, polyurethane, and/or polyureaurethane, in one aspect said polyurea comprises polyoxymethyleneurea and/or melamine formaldehyde; polyolefins; polysaccharides, in one aspect alginate and/or chitosan; gelatin; shellac; epoxy resins; vinyl polymers; water insoluble inorganics; silicone; and mixtures thereof.

In one aspect, of said Polymer Assisted Delivery (PAD) Reservoir system said shell may comprise melamine formaldehyde and/or cross linked melamine formaldehyde.

In one aspect of said Polymer Assisted Delivery (PAD) Reservoir system said shell may be coated by a water-soluble cationic polymer selected from the group that consists of polysaccharides, cationically modified starch and cationically modified guar, polysiloxanes, dimethyldiallylammonium polyhalogenides, copolymers of dimethyldiallylammonium polychloride and vinyl pyrrolidone, acrylamides, imidazoles, imidazolinium halogenides and imidazolium halogenides and polyvinyl amine and its copolymers with N-vinyl formamide.

In one aspect of said Polymer Assisted Delivery (PAD) Reservoir system said coating that coats said shell, may comprise a cationic polymer and an anionic polymer.

In one aspect of said Polymer Assisted Delivery (PAD) Reservoir system wherein said cationic polymer may comprise hydroxyl ethyl cellulose; and said anionic polymer may comprise carboxyl methyl cellulose.

In one aspect, said Polymer Assisted Delivery (PAD) Reservoir system is a fragrance microcapsule.

Process of Making Encapsulates. Suitable processes of making encapsulates as well as suitable shell materials are described in U.S. Pat. No. 6,869,923 B1 and U.S. Published Patent Applications Nos. 2005/0276831 A1 and 2007/020263 A1. Suitable equipment for use in the processes disclosed herein may include continuous stirred tank reactors, homogenizers, turbine agitators, recirculating pumps, paddle mixers, ploughshear mixers, ribbon blenders, vertical axis granulators and drum mixers, both in batch and, where available, in continuous process configurations, spray dryers, and extruders. Such equipment can be obtained from Lodige GmbH (Paderborn, Germany), Littleford Day, Inc. (Florence, Ky., U.S.A.), Forberg AS (Larvik, Norway), Glatt Ingenieurtechnik GmbH (Weimar, Germany), Niro (Soeborg, Denmark), Hosokawa Bepex Corp. (Minneapolis, Minn., U.S.A.), Arde Barinco (New Jersey, U.S.A.).

Adjunct Materials. While not essential for each consumer product embodiment of the present invention, the non-limiting list of adjuncts illustrated hereinafter are suitable for use in the instant consumer products and may be desirably incorporated in certain embodiments of the invention, for example to assist or enhance performance, for treatment of the substrate to be cleaned, or to modify the aesthetics of the composition as is the case with fragrances, colorants, dyes or the like. The precise nature of these additional components, and levels of incorporation thereof, will depend on the physical form of the composition and the nature of the operation for which it is to be used. Such adjunct are in addition to the fragrances and/or fragrance delivery systems previously disclosed herein. Suitable adjunct materials include, but are not limited to, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional fragrance and fragrance delivery systems, structure elasticizing agents, thickeners/structurants, fabric softeners, carriers, hydrotropes, processing aids and/or pigments.

As stated, the adjunct ingredients are not essential for each consumer product embodiment of the present invention. Thus, certain embodiments of the compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional fragrances and fragrance delivery systems, structure elasticizing agents, thickeners/structurants, fabric softeners, carriers, hydrotropes, processing aids and/or pigments. However, when one or more adjuncts is present, such one or more adjuncts may be present as detailed below:

Surfactants. The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders. The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders, polycarboxylate compounds, ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents. The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents. The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants. The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes. The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, ß-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers. Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes. The compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methyl-enephosphonic acid) and water-soluble salts thereof.

If desired, the compositions herein can be catalyzed by means of a manganese compound. Such compounds and levels of use are well known in the art.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Preferred transition-metals in the instant transition-metal bleach catalyst include manganese, iron and chromium. Preferred MRL's herein are a special type of ultra-rigid ligand that is cross-bridged such as 5,12-diethyl-1,5,8,12-tetraazabicyclo[6.6.2]hexa-decane.

Rheology Modifier. The liquid compositions of the present invention may comprise a rheology modifier. The rheology modifier may be selected from the group consisting of non-polymeric crystalline, hydroxy-functional materials, polymeric rheology modifiers which impart shear thinning characteristics to the aqueous liquid matrix of the composition. In one aspect, such rheology modifiers impart to the aqueous liquid composition a high shear viscosity, at 20 sec-1 shear rate and at 21° C., of from 1 to 7000 cps and a viscosity at low shear (0.5 sec-1 shear rate at 21° C.) of greater than 1000 cps, or even 1000 cps to 200,000 cps. In one aspect, for cleaning and treatment compositions, such rheology modifiers impart to the aqueous liquid composition a high shear viscosity, at 20 sec-1 and at 21° C., of from 50 to 3000 cps and a viscosity at low shear (0.5 sec-1 shear rate at 21° C.) of greater than 1000 cps, or even 1000 cps to 200,000 cps. Viscosity according to the present invention is measured using an AR 2000 rheometer from TA instruments using a plate steel spindle having a plate diameter of 40 mm and a gap size of 500 μm. The high shear viscosity at 20 sec-1 and low shear viscosity at 0.5 sec-1 can be obtained from a logarithmic shear rate sweep from 0.1 sec-1 to 25 sec-1 in 3 minutes time at 21° C. Crystalline hydroxyl functional materials are rheology modifiers which form thread-like structuring systems throughout the matrix of the composition upon in situ crystallization in the matrix. Polymeric rheology modifiers are preferably selected from polyacrylates, polymeric gums, other non-gum polysaccharides, and combinations of these polymeric materials.

Generally the rheology modifier will comprise from 0.01% to 1% by weight, preferably from 0.05% to 0.75% by weight, more preferably from 0.1% to 0.5% by weight, of the compositions herein.

Structuring agents which are especially useful in the compositions of the present invention may comprise non-polymeric (except for conventional alkoxylation), crystalline hydroxy-functional materials which can form thread-like structuring systems throughout the liquid matrix when they are crystallized within the matrix in situ. Such materials can be generally characterized as crystalline, hydroxyl-containing fatty acids, fatty esters or fatty waxes. In one aspect, rheology modifiers include crystalline, hydroxyl-containing rheology modifiers include castor oil and its derivatives. In one aspect, rheology modifiers include hydrogenated castor oil derivatives such as hydrogenated castor oil and hydrogenated castor wax. Commercially available, castor oil-based, crystalline, hydroxyl-containing rheology modifiers include THIXCIN™ from Rheox, Inc. (now Elementis).

Other types of rheology modifiers, besides the non-polymeric, crystalline, hydroxyl-containing rheology modifiers described heretofore, may be utilized in the liquid detergent compositions herein. Polymeric materials which provide shear-thinning characteristics to the aqueous liquid matrix may also be employed.

Suitable polymeric rheology modifiers include those of the polyacrylate, polysaccharide or polysaccharide derivative type. Polysaccharide derivatives typically used as rheology modifiers comprise polymeric gum materials. Such gums include pectine, alginate, arabinogalactan (gum Arabic), carrageenan, gellan gum, xanthan gum and guar gum.

If polymeric rheology modifiers are employed herein, a preferred material of this type is gellan gum. Gellan gum is a heteropolysaccharide prepared by fermentation of Pseudomonaselodea ATCC 31461. Gellan gum is commercially marketed by CP Kelco U.S., Inc. under the KELCO-GEL tradename.

A further alternative and suitable rheology modifier include a combination of a solvent and a polycarboxylate polymer. More specifically the solvent may be an alkylene glycol. In one aspect, the solvent may comprise dipropylene glycol. In one aspect, the polycarboxylate polymer may comprise a polyacrylate, polymethacrylate or mixtures thereof. In one aspect, solvent may be present, based on total composition weight, at a level of from 0.5% to 15%, or from 2% to 9% of the composition. In one aspect, polycarboxylate polymer may be present, based on total composition weight, at a level of from 0.1% to 10%, or from 2% to 5%. In one aspect, the solvent component may comprise mixture of dipropylene glycol and 1,2-propanediol. In one aspect, the ratio of dipropylene glycol to 1,2-propanediol may be 3:1 to 1:3, or even 1:1. In one aspect, the polyacrylate may comprise a copolymer of unsaturated mono- or di-carbonic acid and $C_1$-$C_{30}$ alkyl ester of the (meth) acrylic acid. In another aspect, the rheology modifier may comprise a polyacrylate of unsaturated mono- or di-carbonic acid and $C_1$-$C_{30}$ alkyl ester of the (meth) acrylic acid. Such copolymers are available from Noveon Inc. under the tradename Carbopol Aqua 30®.

In the absence of rheology modifier and in order to impart the desired shear thinning characteristics to the liquid composition, the liquid composition can be internally structured through surfactant phase chemistry or gel phases.

7. Processes of Making and Using Consumer Products

The embodiments of consumer products of the present invention can be formulated into any suitable form and prepared by any process chosen by the formulator, non-limiting examples of which are described in U.S. Pat. No. 5,879,584; which is incorporated herein by reference.

7.1 Fabric/Home Care: Cleaning and/or Treatment Compositions

In one aspect of the presently disclosed consumer product, said consumer product is a cleaning and/or treatment composition, said composition typically comprises an ingredient selected from the group consisting of builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, hueing dyes, fragrances, fragrance delivery systems, structure elasticizing agents, carriers, structurants, hydrotropes, processing aids, solvents in addition to said solubilizing agent, a fabric softener active selected from the group consisting of a silicone polymer, a polysaccharide, a clay, a fatty ester, a dispersible polyolefin, a polymer latex and mixtures thereof, pigments, and mixtures thereof, preferably said composition comprises an organic acid, preferably citric acid and/or lactic acid, hydrogenated castor oil, ethoxylated polyethleneimines, preferably PEI 600 EO 20 and/or PEI 600, an enzyme, preferably a cold water amylase, cold water protease and/or xylogluconase.

In one aspect of the cleaning and/or treatment composition, said cleaning and/or treatment composition comprises a fabric softener active is selected from the group consisting of a quaternary ammonium compound, a silicone polymer, a polysaccharide, a clay, an amine, a fatty ester, a dispersible polyolefin, a polymer latex and mixtures thereof, preferably
  a. said quaternary ammonium compound comprises an alkyl quaternary ammonium compound, preferably said alkyl quaternary ammonium compound is selected from the group consisting of a monoalkyl quaternary ammonium compound, a dialkyl quaternary ammonium compound, a trialkyl quaternary ammonium compound and mixtures thereof;
  b. said silicone polymer is selected from the group consisting of cyclic silicones, polydimethylsiloxanes, aminosilicones, cationic silicones, silicone polyethers, silicone resins, silicone urethanes, and mixtures thereof;
  c. said polysaccharide comprises a cationic starch;
  d. said clay comprises a smectite clay;
  e. said dispersible polyolefin is selected from the group consisting of polyethylene, polypropylene and mixtures thereof; and
  f. said fatty ester is selected from the group consisting of a polyglycerol ester, a sucrose ester, a glycerol ester and mixtures thereof.

In one aspect of the cleaning and/or treatment composition, said cleaning and/or treatment composition comprises a fabric softener active comprising a material selected from the group consisting of monoesterquats, diesterquats, triesterquats, and mixtures thereof, preferably, said monoesterquats and diesterquats are selected from the group consisting of bis-(2-hydroxypropyl)-dimethylammonium methylsulfate fatty acid ester and isomers of bis-(2-hydroxypropyl)-dimethylammonium methylsulfate fatty acid ester and/or mixtures thereof, 1,2-di(acyloxy)-3-trimethylammoniopropane chloride, N,N-bis(stearoyl-oxy-ethyl)-N,N-dimethyl ammonium chloride, N,N-bis(tallowoyl-oxy-ethyl)-N,N-dimethyl ammonium chloride, N,N-bis(stearoyl-oxy-ethyl)-N-(2-hydroxyethyl)-N-methyl ammonium methyl sulfate, N,N-bis-(stearoyl-2-hydroxypropyl)-N,N-dimethylammonium methyl sulfate, N,N-bis-(tallowoyl-2-hydroxypropyl)-N,N-dimethylammonium methyl sulfate, N,N-bis-(palmitoyl-2-hydroxypropyl)-N,N-dimethylammonium methyl sulfate, N,N-bis-(stearoyl-2-hydroxypropyl)-N,N-dimethylammonium chloride, 1,2-di-(stearoyl-oxy)-3-trimethyl ammoniumpropane chloride, dicanoladimethylammonium chloride, di(hard)tallowdimethylammonium chloride, dicanoladimethylammonium methylsulfate, 1-methyl-1-stearoylamidoethyl-2-stearoylimidazolinium methylsulfate, 1-tallowylamidoethyl-2-tallowylimidazoline, dipalmylmethyl hydroxyethylammoinum methylsulfate and mixtures thereof.

In one aspect of the cleaning and/or treatment composition, said composition comprises a quaternary ammonium compound and a silicone polymer, preferably said composition comprises from 0.001% to 10%, from 0.1% to 8%, more preferably from 0.5% to 5%, of said silicone polymer.

In one aspect of the cleaning and/or treatment composition, said fabric softening active has an Iodine Value of between 0-140, preferably 5-100, more preferably 10-80, even more preferably, 15-70, most preferably 18-25 or when said fabric softening active comprises a partially hydrogenated fatty acid quaternary ammonium compound said fabric softening active most preferably has a Iodine Value of 25-60.

In one aspect of the cleaning and/or treatment composition, said cleaning and/or treatment composition is a soluble unit-dose product said soluble unit dose product comprising one or more cleaning and/or treatment compositions contained within one or more chambers said chambers being formed from one or more films, preferably said one or more films comprise PVA film.

7.2 Antiperspirant Compositions

Antiperspirant compositions can be formulated in many forms. For example an antiperspirant composition can be, without limitation, a roll on product, a body spray, a stick including soft solid sticks and invisible solids, or an aerosol. Each of the antiperspirant compositions described below can include fragrance materials as described herein.

7.2.1 Roll-On and Clear Gel

A roll-on antiperspirant composition can comprise, for example, water, emollient, solubilizer, deodorant actives, antioxidants, preservatives, or combinations thereof. A clear gel antiperspirant composition can comprise, for example, water, emollient, solubilizer, deodorant actives, antioxidants, preservatives, ethanol, or combinations thereof.

Water. The roll-on composition can include water. Water can be present in an amount of about 1% to about 99.5%, about 25% to about 99.5%, about 50% to about 99.5%, about 75% to about 99.5% about 80% to about 99.5%, from about 15% to about 45%, or any combination of the end points and points encompassed within the ranges, by weight of the deodorant composition.

Emollients. Roll-on compositions can comprise an emollient system including at least one emollient, but it could also be a combination of emollients. Suitable emollients are often liquid under ambient conditions. Depending on the type of product form desired, concentrations of the emollient(s) in the deodorant compositions can range from about 1% to about 95%, from about 5% to about 95%, from about 15% to about 75%, from about 1% to about 10%, from about 15% to about 45%, or from about 1% to about 30%, by weight of the deodorant composition.

Emollients suitable for use in the roll-on compositions include, but are not limited to, propylene glycol, polypropylene glycol (like dipropylene glycol, tripropylene glycol, etc.), diethylene glycol, triethylene glycol, PEG-4, PEG-8, 1,2 pentanediol, 1,2 hexanediol, hexylene glycol, glycerin, $C_2$ to $C_{20}$ monohydric alcohols, $C_2$ to $C_{40}$ dihydric or polyhydric alcohols, alkyl ethers of polyhydric and monohydric alcohols, volatile silicone emollients such as cyclopentasiloxane, nonvolatile silicone emollients such as dimethicone, mineral oils, polydecenes, petrolatum, and combinations thereof. One example of a suitable emollient comprises PPG-15 stearyl ether. Other examples of suitable emollients include dipropylene glycol and propylene glycol.

Deodorant Actives. Suitable deodorant actives can include any topical material that is known or otherwise effective in preventing or eliminating malodor associated with perspiration. Suitable deodorant actives may be selected from the group consisting of antimicrobial agents (e.g., bacteriocides, fungicides), malodor-absorbing material, and combinations thereof. For example, antimicrobial agents may comprise cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof. The concentration of the optional deodorant active may range from about 0.001%, from about 0.01%, of from about 0.1%, by weight of the composition to about 20%, to about 10%, to about 5%, or to about 1%, by weight of the composition.

Odor Entrappers. The composition can include an odor entrapper. Suitable odor entrappers for use herein include, for example, solubilized, water-soluble, uncomplexed cyclodextrin. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in a donut-shaped ring. The specific coupling and conformation of the glucose units give the cyclodextrins a rigid, conical molecular structure with a hollow interior of a specific volume. The "lining" of the internal cavity is formed by hydrogen atoms and glycosidic bridging oxygen atoms, therefore this surface is fairly hydrophobic. The unique shape and physical-chemical property of the cavity enable the cyclodextrin molecules to absorb (form inclusion complexes with) organic molecules or parts of organic molecules which can fit into the cavity. Many fragrance molecules can fit into the cavity.

Cyclodextrin molecules are described in U.S. Pat. Nos. 5,714,137, and 5,942,217. Suitable levels of cyclodextrin are from about 0.1% to about 5%, alternatively from about 0.2% to about 4%, alternatively from about 0.3% to about 3%, alternatively from about 0.4% to about 2%, by weight of the composition.

Buffering Agent. The composition can include a buffering agent which may be alkaline, acidic or neutral. The buffer can be used in the composition for maintaining the desired pH. The composition may have a pH from about 3 to about 10, from about 4 to about 9, from about 5 to about 8, from about 6 to about 7, or it may have a pH of about 6.5. One unique feature of the polyvinyl amine malodor control polymers is its ability to maintain active nitrogen sites at high pH levels which can help enhance the antibacterial effect which comes, at least in part, from the nitrogen sites.

Suitable buffering agents include, for example, hydrochloric acid, sodium hydroxide, potassium hydroxide, and combinations thereof.

The compositions can contain at least about 0%, alternatively at least about 0.001%, alternatively at least about 0.01%, by weight of the composition, of a buffering agent. The composition may also contain no more than about 1%, alternatively no more than about 0.75%, alternatively no more than about 0.5%, by weight of the composition, of a buffering agent.

Solubilizer. The composition can contain a solubilizer. A suitable solubilizer can be, for example, a surfactant, such as a no-foaming or low-foaming surfactant. Suitable surfactants are nonionic surfactants, cationic surfactants, amphoteric surfactants, zwitterionic surfactants, and mixtures thereof.

Suitable solubilizers include, for example, hydrogenated castor oil, polyoxyethylene 2 stearyl ether, polyoxyethylene 20 stearyl ether, and combinations thereof. One suitable hydrogenated castor oil that may be used in the present composition is polyoxyethylene hydrogenated castor oil.

When the solubilizing agent is present, it is typically present at a level of from about 0.01% to about 5%, alternatively from about 0.01% to about 3%, alternatively from about 0.05% to about 1%, alternatively from about 0.01% to about 0.05%, by weight of the composition.

Preservatives. The composition can include a preservative. The preservative is included in an amount sufficient to prevent spoilage or prevent growth of inadvertently added microorganisms for a specific period of time, but not sufficient enough to contribute to the odor neutralizing performance of the composition. In other words, the preservative is not being used as the antimicrobial compound to kill microorganisms on the surface onto which the composition is deposited in order to eliminate odors produced by microorganisms. Instead, it is being used to prevent spoilage of the composition in order to increase shelf-life.

The preservative can be any organic preservative material which will not cause damage to fabric appearance, e.g., discoloration, coloration, bleaching. Suitable water-soluble preservatives include organic sulfur compounds, halogenated compounds, cyclic organic nitrogen compounds, low molecular weight aldehydes, parabens, propane diol materials, isothiazolinones, quaternary compounds, benzoates, low molecular weight alcohols, dehydroacetic acid, phenyl and phenoxy compounds, or mixtures thereof.

Non-limiting examples of commercially available water-soluble preservatives include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxy-methyl) urea, commonly known as diazolidinyl urea, available under the trade name Germall® II from Sutton Laboratories, Inc.; N,N"-methylenebis{N'[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from Sutton Laboratories, Inc.; polymethoxy bicyclic oxazolidine, available under the trade name Nuosept® C from Hills America; formaldehyde; glutaraldehyde; polyaminopropyl biguanide, available under the trade name Cosmocil CQ® from ICI Americas, Inc., or under the trade name Mikrokill® from Brooks, Inc.; dehydroacetic acid; and benzsiothiazolinone available under the trade name Koralone™ B-119 from Rohm and Hass Corporation.

Suitable levels of preservative can range from about 0.0001% to about 0.5%, alternatively from about 0.0002% to about 0.2%, alternatively from about 0.0003% to about 0.1%, by weight of the composition.

7.2.2 Body Spray

A body spray can contain, for example, a carrier, fragrance, a deodorant active, odor entrappers, propellant, or combinations thereof. The body spray compositions can be applied as a liquid.

Carrier. A carrier suitable for use in a body spray can include, water, alcohol, or combinations thereof. The carrier may be present in an amount of about 1% to about 99.5%, about 25% to about 99.5%, about 50% to about 99.5%, about 75% to about 99.5% about 80% to about 99.5%, from about 15% to about 45%, or any combination of the end points and points encompassed within the ranges, by weight of the composition. A suitable example of an alcohol can include ethanol.

Propellant. The compositions described herein can include a propellant. Some examples of propellants include compressed air, nitrogen, inert gases, carbon dioxide, and mixtures thereof. Propellants may also include gaseous hydrocarbons like propane, n-butane, isobutene, cyclopropane, and mixtures thereof. Halogenated hydrocarbons like 1,1-difluoroethane may also be used as propellants. Some non-limiting examples of propellants include 1,1,1,2,2-pentafluoroethane, 1,1,1,2-tetrafluoroethane, 1,1,1,2,3,3,3-heptafluoropropane, trans-1,3,3,3-tetrafluoroprop-1-ene, dimethyl ether, dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof. Some other propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), and 152A (1,1 diflouroethane). The propellant may have a concentration from about 15%, 25%, 30%, 32%, 34%, 35%, 36%, 38%, 40%, or 42% to about 70%, 65%, 60%, 54%, 52%, 50%, 48%, 46%, 44%, or 42%, or any combination thereof, by weight of the total fill of materials stored within the container.

7.2.3 Invisible Solid

Invisible solid antiperspirant compositions as described herein can contain a primary structurant, an antiperspirant active, a fragrance, and additional chassis ingredient(s). The antiperspirant composition can further comprise other optional ingredient(s). The compositions can be in the form of a solid stick. The compositions can have a product hardness of about 600 gram force or more. The compositions may be free of dipropylene glycol, added water, castor wax, or any combination thereof. The antiperspirant composition may be anhydrous. The antiperspirant composition may be free of added water.

Hardness. The invisible solid can have a product hardness of least about 600 gram·force, more specifically from about 600 gram·force to about 5,000 gram·force, still more specifically from about 750 gram·force to about 2,000 gram·force, and yet more specifically from about 800 gram·force to about 1,400 gram·force.

The term "product hardness" or "hardness" as used herein is a reflection of how much force is required to move a penetration cone a specified distance and at a controlled rate into an antiperspirant composition under the test conditions described herein below. Higher values represent harder product, and lower values represent softer product. These values are measured at 27° C., 15% relative humidity, using a TA-XT2 Texture Analyzer, available from Texture Technology Corp., Scarsdale, N.Y., U.S.A. The product hardness value as used herein represents the peak force required to move a standard 45-degree angle penetration cone through the composition for a distance of 10 mm at a speed of 2 mm/second. The standard cone is available from Texture Technology Corp., as part number TA-15, and has a total cone length of about 24.7 mm, angled cone length of about 18.3 mm, and a maximum diameter of the angled surface of the cone of about 15.5 mm. The cone is a smooth, stainless steel construction and weighs about 17.8 grams.

Primary Structurants. The invisible solid can comprise a suitable concentration of a primary structurant to help provide the antiperspirant with the desired viscosity, rheology, texture and/or product hardness, or to otherwise help suspend any dispersed solids or liquids within the composition.

The term "solid structurant" as used herein means any material known or otherwise effective in providing suspending, gelling, viscosifying, solidifying, and/or thickening properties to the composition or which otherwise provide structure to the final product form. These solid structurants include gelling agents, and polymeric or non-polymeric or inorganic thickening or viscosifying agents. Such materials will typically be solids under ambient conditions and include organic solids, crystalline or other gellants, inorganic particulates such as clays or silicas, or combinations thereof.

The concentration and type of solid structurant selected for use in the antiperspirant compositions will vary depending upon the desired product hardness, rheology, and/or other related product characteristics. For most structurants suitable for use herein, the total structurant concentration ranges from about 5% to about 35%, more typically from about 10% to about 30%, or from about 7% to about 20%, by weight of the composition.

Non-limiting examples of suitable primary structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fischer-Tropsch waxes, and microcrystalline wax; polyethylenes with molecular weight of 200 to 1000 Daltons; solid triglycerides; behenyl alcohol, or combinations thereof.

Other non-limiting examples of primary structurants suitable for use herein are described in U.S. Pat. Nos. 5,976,514 and 5,891,424, the descriptions of which are incorporated herein by reference.

Antiperspirant Active. The antiperspirant stick compositions can comprise a particulate antiperspirant active suitable for application to human skin. The concentration of antiperspirant active in the composition should be sufficient to provide the desired perspiration wetness and odor control from the antiperspirant stick formulation selected.

The antiperspirant stick compositions can comprise an antiperspirant active at concentrations of from about 0.5% to about 60%, and more specifically from about 5% to about 35%, by weight of the composition. These weight percentages are calculated on an anhydrous metal salt basis exclusive of water and any complexing agents such as, for example, glycine, and glycine salts. The antiperspirant active as formulated in the composition can be in the form of dispersed particulate solids having an average particle size or equivalent diameter of less than about 100 microns, more specifically less than about 20 microns, and even more specifically less than about 10 microns.

The antiperspirant active for use in the anhydrous antiperspirant compositions of the present invention can include any compound, composition or other material having antiperspirant activity. More specifically, the antiperspirant actives may include astringent metallic salts, especially inorganic and organic salts of aluminum, zirconium and zinc, as well as mixtures thereof. Even more specifically, the antiperspirant actives may include aluminum-containing and/or zirconium-containing salts or materials, such as, for example, aluminum halides, aluminum chlorohydrate, aluminum hydroxyhalides, zirconyl oxyhalides, zirconyl hydroxyhalides, and mixtures thereof.

Aluminum salts for use in the anhydrous antiperspirant stick compositions include those that conform to the formula:

$$Al_2(OH)_aCl_b \cdot xH_2O,$$

wherein a is from about 2 to about 5;
the sum of a and b is about 6;
x is from about 1 to about 6; and
a, b, and x may have non-integer values.

More specifically, aluminum chlorohydroxides referred to as "5/6 basic chlorohydroxide" can be used, wherein a=5, and "2/3 basic chlorohydroxide", wherein a=4.

Processes for preparing aluminum salts are disclosed in U.S. Pat. Nos. 3,887,692; 3,904,741; 4,359,456; and British Patent Specification 2,048,229, the disclosures of which are incorporated herein by reference for the purpose of describing processes for preparing aluminum salts.

Mixtures of aluminum salts are described in British Patent Specification 1,347,950, which description is also incorporated herein by reference.

Zirconium salts for use in the anhydrous antiperspirant stick compositions include those which conform to the formula:

$$ZrO(OH)_{2-a}Cl_a \cdot xH_2O,$$

wherein a is from about 1.5 to about 1.87;
x is from about 1 to about 7; and
a and x may both have non-integer values.

These zirconium salts are described in Belgian Patent 825,146, Schmitz, issued Aug. 4, 1975, which description is incorporated herein by reference. Zirconium salts that additionally contain aluminum and glycine, commonly known as "ZAG complexes," are believed to be especially beneficial. These ZAG complexes contain aluminum chlorohydroxide and zirconyl hydroxy chloride conforming to the above-described formulas. Such ZAG complexes are described in U.S. Pat. No. 3,792,068; Great Britain Patent Application 2,144,992; and U.S. Pat. No. 4,120,948, disclosures of which are incorporated herein by reference for the limited purpose of describing ZAG complexes.

Also suitable for use herein are enhanced efficacy aluminum-zirconium chlorohydrex-amino acid which typically has the empirical formula $Al_nZr(OH)_{[3n+4-m(n+1)]}(Cl)_{[m(n+1)]}$-$AA_q$ where n is 2.0 to 10.0, preferably 3.0 to 8.0; m is about 0.48 to about 1.11 (which corresponds to M:Cl approximately equal to 2.1-0.9), preferably about 0.56 to about 0.83 (which corresponds to M:Cl approximately equal to 1.8-1.2); q is about 0.8 to about 4.0, preferably about 1.0 to 2.0; and AA is an amino acid such as glycine, alanine, valine, serine, leucine, isoleucine, β-alanine, cysteine, β-amino-n-butyric acid, or γ-amino-n-butyric acid, preferably glycine. These salts also generally have some water of hydration associated with them, typically on the order of 1 to 5 moles per mole of salt (typically, about 1% to about 16%, more typically about 4% to about 13% by weight). These salts are generally referred to as aluminum-zirconium trichlorohydrex or tetrachlorohydrex when the Al:Zr ratio is between 2 and 6 and as aluminum-zirconium pentachlorohydrex or octachlorohydrex when the Al:Zr ratio is between 6 and 10. The term "aluminum-zirconium chlorohydrex" is intended to embrace all of these forms. The preferred aluminum-zirconium salt is aluminum-zirconium chlorohydrex-glycine. Additional examples of suitable high efficacy antiperspirant actives can include Aluminum Zirconium Pentachlorohydrex Glycine, Aluminum Zirconium Octachlorohydrex Glycine, or a combination thereof. These high efficacy actives are more fully described in U.S. App. Pub. No. 2007/0003499 by Shen et al. filed Jun. 30, 2005.

7.2.4 Additional Chassis Ingredients

Additional Structurant. The antiperspirant composition can further comprise an additional structurant. The additional structurant may be present in an amount from 1% to about 10%, by weight of the composition. The additional structurant(s) will likely be present at an amount less than the primary structurant.

Non-limiting examples of suitable additional structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fisher-Tropsch waxes, and microcrystalline wax; polyethylenes with molecular weight of 200 to 1000 daltons; and solid triglycerides; behenyl alcohol, or combinations thereof.

Other non-limiting examples of additional structurants suitable for use herein are described in U.S. Pat. Nos. 5,976,514 and 5,891,424.

Solvent. The antiperspirant composition can comprise a solvent at concentrations ranging from about 20% to about 80%, and more specifically from about 30% to about 70%, by weight of the composition. The solvent can be a volatile silicone which may be cyclic or linear.

"Volatile silicone" as used herein refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976), which descriptions are incorporated herein by reference.

The volatile silicone can be a cyclic silicone having from 3 to 7, and more specifically from 5 to 6, silicon atoms, and still more specifically 5, like cyclopentasiloxane. These cyclic silicone materials will generally have viscosities of less than about 10 centistokes at 25° C.

Linear volatile silicone materials suitable for use in the antiperspirant compositions include those represented by the formula:

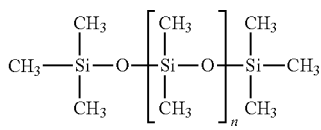

wherein n is from 1 to 7, and more specifically from 2 to 3. These linear silicone materials will generally have viscosities of less than about 5 centistokes at 25° C.

Specific examples of volatile silicone solvents suitable for use in the antiperspirant compositions include, but are not limited to, Cyclomethicone D-5; GE 7207 and GE 7158 (commercially available from General Electric Co.); Dow Corning 344; Dow Corning 345; Dow Corning 200; and DC1184 (commercially available from Dow Corning Corp.); and SWS-03314 (commercially available from SWS Silicones).

Non-Volatile Organic Fluids. Non-volatile organic fluids may be present, for example, in an amount of about 15% or less, by weight of the composition.

Non-limiting examples of nonvolatile organic fluids include mineral oil, PPG-14 butyl ether, isopropyl myristate, petrolatum, butyl stearate, cetyl octanoate, butyl myristate, myristyl myristate, C12-15 alkylbenzoate (e.g., Finsolv™), octyldodecanol, isostearyl isostearate, octododecyl benzoate, isostearyl lactate, isostearyl palmitate, and isobutyl stearate.

Adjunct Ingredients. The anhydrous antiperspirant compositions can further comprise any optional material that is known for use in antiperspirant and deodorant compositions or other personal care products, or which is otherwise suitable for topical application to human skin.

One example of optional materials are clay mineral powders such as talc, mica, sericite, silica, magnesium silicate, synthetic fluorphlogopite, calcium silicate, aluminum silicate, bentonite and montomorillonite; pearl pigments such as alumina, barium sulfate, calcium secondary phosphate, calcium carbonate, titanium oxide, finely divided titanium oxide, zirconium oxide, zinc oxide, hydroxy apatite, iron oxide, iron titrate, ultramarine blue, Prussian blue, chromium oxide, chromium hydroxide, cobalt oxide, cobalt titanate, titanium oxide coated mica; organic powders such as polyester, polyethylene, polystyrene, methyl methacrylate resin, cellulose, 12-nylon, 6-nylon, styrene-acrylic acid copolymers, poly propylene, vinyl chloride polymer, tetrafluoroethylene polymer, boron nitride, fish scale guanine, laked tar color dyes, laked natural color dyes; and combinations thereof.

Talc, if used at higher levels can produce a significant amount of white residue which has been found to be a consumer negative for product acceptance. Therefore it is best to limit the composition to less than 10%, less than about 8%, less than about 6%, or less than about 3%, by weight of the composition.

Nonlimiting examples of other optional materials include emulsifiers, distributing agents, antimicrobials, pharmaceutical or other topical active, preservatives, surfactants, and so forth. Examples of such optional materials are described in U.S. Pat. Nos. 4,049,792; 5,019,375; and 5,429,816; which descriptions are incorporated herein by reference.

7.2.5 Soft Solid

Soft solid composition can comprise volatile silicone, antiperspirant active, gellant, residue masking material, or combinations thereof. In addition, soft solids generally have a hardness value after dispensing of about 500 gram force or less.

Volatile Silicone Solvent. The soft solid can comprises a volatile silicone solvent at concentrations ranging from about 20% to about 80%, preferably from about 30% to about 70%, more preferably from about 45% to about 70%, by weight of the composition. The volatile silicone of the solvent may be cyclic or linear.

"Volatile silicone" as used herein refers to those silicone materials which have measurable vapor pressure under ambient conditions. Nonlimiting examples of suitable volatile silicones are described in Todd et al., "Volatile Silicone Fluids for Cosmetics", Cosmetics and Toiletries, 91:27-32 (1976), which descriptions are incorporated herein by reference. Preferred volatile silicone materials are those having from about 3 to about 7, preferably from about 4 to about 5, silicon atoms.

Cyclic volatile silicones are preferred for use in the antiperspirant compositions herein, and include those represented by the formula:

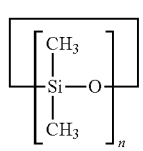

wherein n is from about 3 to about 7, preferably from about 4 to about 5, most preferably 5. These cyclic silicone materials will generally have viscosities of less than about 10 centistokes at 25° C.

Linear volatile silicone materials suitable for use in the antiperspirant compositions include those represented by the formula:

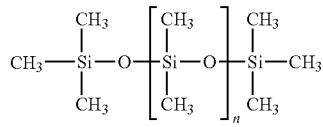

wherein n is from about 1 to about 7, preferably from about 2 to about 3. These linear silicone materials will generally have viscosities of less than about 5 centistokes at 25° C.

Specific examples of volatile silicone solvents suitable for use in the antiperspirant compositions include, but are not limited to, Cyclomethicone D-5 (commercially available from G. E. Silicones), Dow Corning 344, Dow Corning 345 and Dow Corning 200 (commercially available from Dow Corning Corp.), GE 7207 and 7158 (commercially available from General Electric Co.) and SWS-03314 (commercially available from SWS Silicones Corp.).

Gellant Material. The soft solid can include a gellant material comprising fatty alcohols having from about 20 to about 60 carbon atoms, or combinations thereof, at concentrations ranging from about 0.1% to about 8% by weight of the composition. The gellant material, when combined with the volatile silicone solvent described herein before, provides the composition with a physically stable structure within which the particulate antiperspirant materials are dispersed, and maintained as such over an extended period of time.

Specifically, the gellant material can comprise saturated or unsaturated, substituted or unsubstituted, fatty alcohols or mixtures of fatty alcohols having from about 20 to about 60 carbons atoms, preferably from about 20 to about 40 carbon atoms. Preferred are combinations of the fatty alcohols. The fatty alcohol gellants are preferably saturated, unsubstituted monohydric alcohols or combinations thereof, which have a melting point of at less than about 110° C., more preferably from about 60° to about 110° C., even more preferably between about 100° C. and 110° C.

It has been found that this fatty alcohol-based gellant material, when combined with volatile silicone solvents provides a stable structure for maintaining a dispersion of particulate antiperspirant material in a topical formulation without the necessity of using conventional particulate thickening agents. This gellant material is especially useful in maintaining the physical stability of particulate dispersions containing higher concentrations of volatile silicone solvents.

It was also found that penetration force values for the antiperspirant compositions can be controlled by adjusting total fatty alcohol concentrations. In controlling penetration force values in this manner, there is no longer a need to use organic solvents or thickening agents to control penetration force values, which solvents or thickening agents often add cost to the formulation, introduce additional compatibility issues, and often contribute undesirable cosmetics such as prolonged stickiness, difficulty in ease of spreading, increased dry-down times and reduced dry feel after application.

Specific concentrations of the gellant materials can be selected according to the desired penetration force value. For roll-on formulations having a penetration force value of from about 20 gram·force to about 100 gram·force, gellant material concentrations preferably range from about 0.1% to about 3%, preferably from about 1.5% to about 3%, by weight of the antiperspirant composition. For other cream formulations, including those formulations suitable for use in cream applicator devices, which have a penetration force value of from about 100 gram·force to about 500 gram·force, gellant material concentrations preferably range from about 3% to about 8%, preferably from about 3% to about 6%, by weight of the antiperspirant composition.

Specific examples of fatty alcohol gellants for use in the antiperspirant compositions that are commercially available include, but are not limited to, Unilin® 425, Unilin® 350, Unilin® 550 and Unilin® 700 (supplied by Petrolite)

Residue Masking Material. The soft solid compositions can further comprise a nonvolatile emollient as a residue masking material Such materials and their use in antiperspirant products are well known in the antiperspirant art, and any such material may be incorporated into the composition of the present invention, provided that such optional material is compatible with the essential elements of the composition, or does not unduly impair product performance or cosmetics.

Concentrations of the optional residue masking material can range from about 0.1% to about 40%, preferably from about 1% to about 10%, by weight of the antiperspirant composition. These optional materials can be liquid at ambient temperatures, and can be nonvolatile. The term "nonvolatile" as used in this context refers to materials which have a boiling point under atmospheric pressure of at least about 200° C. Nonlimiting examples of suitable residue masking materials for use in the antiperspirant products include butyl stearate, diisopropyl adipate, petrolatum, nonvolatile silicones, octyldodecanol, phenyl trimethicone, isopropyl myristate, C12-15 ethanol benzoates and PPG-14 Butyl Ether. Residue masking materials are described, for example, in U.S. Pat. No. 4,985,238, which description is incorporated herein by reference.

Other Materials. The soft solid compositions can further comprise one, or more, other materials which modify the physical characteristics of the compositions or serve as additional "active" components when deposited on the skin. Many such materials are known in the antiperspirant art and can be used in the antiperspirant compositions herein, provided that such optional materials are compatible with the essential materials described herein, or do not otherwise unduly impair product performance.

Non limiting examples of materials can include active components such as bacteriostats and fungiostats, and "nonactive" components such as colorants, fragrances, cosmetic powders, emulsifiers, chelants, distributing agents, preservatives, and wash-off aids. Examples of such optional materials are described in U.S. Pat. No. 4,049,792; Canadian Patent 1,164,347; U.S. Pat. Nos. 5,019,375; and 5,429,816; which descriptions are incorporated herein by reference.

7.2.6 Aerosol

An aerosol composition can comprise a concentrate, a propellant, or a combination thereof. Alcohol is a predominant component of the concentrates provided herein. Useful alcohols include $C_1$-$C_3$ alcohols, with the preferred alcohol being ethanol. In certain examples, the alcohol is employed at a concentration level of from at least about 40%, 50% or 55% to about 80%, by weight of the concentrate.

An antiperspirant active is dissolved in the alcohol, at a level of from about 1% to about 15%, by weight of the concentrate. Various antiperspirant actives can be employed, including, for example, aluminum chloride, aluminum chlorohydrate, aluminum chlorohydrex, aluminum chlorohydrex PG, aluminum chlorohydrex PEG, aluminum dichlorohydrate, aluminum dichlorohydrex PG, aluminum dichlorohydrex PEG, aluminum sesquichlorohydrate, aluminum sesquichlorohydrex PG, aluminum sesquichlorohydrex PEG, aluminum sulfate, aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorohydrate, aluminum zirconium trichlorohydrate, aluminum zirconium tetrachlorohydrate GLY, and aluminum zirconium trichlorohydrate GLY. In one example, aluminum chlorohydrex PG is the chosen antiperspirant active.

The antiperspirant concentrates can also include an oil or a mixture of two or more oils. Useful oils include, for example, volatile silicone oils and non-volatile organic oils. "Volatile silicone", as used herein, refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976). The volatile silicone can be a cyclic silicone having from at least about 3 silicone atoms or from at least about 5 silicone atoms but no more than about 7 silicone atoms or no more than about 6 silicone atoms. For example, volatile silicones can be used which conform to the formula:

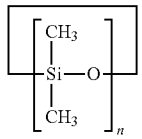

wherein n is from about 3 or from about 5 but no more than about 7 or no more than about 6. These volatile cyclic silicones generally have a viscosity of less than about 10 centistokes at 25° C. Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). SWS-03314, SWS-03400, F-222, F-223, F-250, F-251 (available from SWS Silicones Corp.); Volatile Silicones 7158, 7207, 7349 (available from Union Carbide); MASIL SF-V (available from Mazer) and combinations thereof. Suitable volatile silicone oils can also include linear silicone oils such as, for example, DC200 (1 cSt), DC200 (0.65 cSt), and DC2-1184, all of which are available from Dow Corning Corp. In certain examples, the volatile silicone oil can have a viscosity of less than 10 centistokes at 25° C.

Non-volatile organic, emollient oils can also be employed. A representative, non-limiting list of emollient oils includes CETIOL CC (dicaprylyl carbonate), CETIOL OE (dicaprylyl ether), CETIOL S (diethylhexylcyclohexane), and CETIOL B (dibutyl adipate), all of which are available from Cognis, and LEXFEEL 7 (neopentyl glycol diheptanoate) from Inolex. In certain examples, the organic emollient oils have a viscosity of less than 50 centistokes at 25° C. The term "organic emollient oil" as used herein means silicon-free emollient oils that are liquid at 25° C., and that are safe and light to skin and can be miscible with volatile silicone oils (as described above) and the antiperspirant active-alcohol solution in the concentration ranges described below.

The oil or mixture of oils is generally included in the concentrate formulas at a level of from about 5% to about 45%, by weight of the concentrate. This viscosity ranges noted above in connection with the different classes of oil can facilitate desired spray rates and patterns, and can help minimize nozzle clogging. To provide desired skin feel, minimal nozzle clogging, and good concentrate stability, the ratio of alcohol to volatile silicone oil is preferably greater than 1.0, 1.35, or 1.5. And in examples having both a volatile silicone oil and an organic emollient oil, the ratio of alcohol to total oil is preferably greater than or equal to about 0.90. The oils in certain examples are miscible with the alcohol and antiperspirant active solution. Although various levels of miscibility are acceptable, the oils are preferably miscible enough with the alcohol and antiperspirant active solution to yield a concentrate having a clear appearance.

The antiperspirant compositions can also include residue-masking agents and propellants as discussed above.

7.3 Personal Care Compositions

Personal care compositions can include, but are not limited to, structurants, humectants, fatty acids, inorganic salts, and other antimicrobial agents or actives.

A personal care composition can also include hydrophilic structurants such as carbohydrate structurants and gums. Some suitable carbohydrate structurants include raw starch (corn, rice, potato, wheat, and the like) and pregelatinized starch. Some suitable gums include carrageenan and xanthan gum. A personal care composition can include from about 0.1% to about 30%, from about 2% to about 25%, or from about 4% to about 20%, by weight of the personal care composition, of a carbohydrate structurant.

A personal care composition can also include one or more humectants. Examples of such humectants can include polyhydric alcohols. Further, humectants such as glycerin can be included the personal care composition as a result of production or as an additional ingredient. For example, glycerin can be a by-product after saponification of the personal care composition. Including additional humectant can result in a number of benefits such as improvement in hardness of the personal care composition, decreased water activity of the personal care composition, and reduction of a weight loss rate of the personal care composition over time due to water evaporation.

A personal care composition can include inorganic salts. Inorganic salts can help to maintain a particular water content or level of the personal care composition and improve hardness of the personal care composition. The inorganic salts can also help to bind the water in the personal care composition to prevent water loss by evaporation or other means. A personal care composition can optionally include from about 0.01% to about 15%, from about 1% to about 12%, or from about 2.5% to about 10.5%, by weight of the personal care composition, of inorganic salt. Examples of suitable inorganic salts can include magnesium nitrate, trimagnesium phosphate, calcium chloride, sodium carbonate, sodium aluminum sulfate, disodium phosphate, sodium polymetaphosphate, sodium magnesium succinate, sodium tripolyphosphate, aluminum sulfate, aluminum chloride, aluminum chlorohydrate, aluminum-zirconium trichlorohydrate, aluminum-zirconium trichlorohydrate glycine complex, zinc sulfate, ammonium chloride, ammonium phosphate, calcium acetate, calcium nitrate, calcium phosphate, calcium sulfate, ferric sulfate, magnesium chloride, magnesium sulfate, and tetrasodium pyrophosphate.

A personal care composition can include one or more additional antibacterial agents that can serve to further enhance antimicrobial effectiveness of the personal care composition. A personal care composition can include, for example, from about 0.001% to about 2%, from about 0.01% to about 1.5%, or from about 0.1% to about 1%, by weight of the personal care composition, of additional antibacterial agent(s). Examples of suitable antibacterial agents can include carbanilides, triclocarban (also known as trichlorocarbanilide), triclosan, a halogenated diphenylether available as DP-300 from Ciba-Geigy, hexachlorophene, 3,4,5-tribromosalicylanilide, and salts of 2-pyridinethiol-1-oxide, salicylic acid, and other organic acids. Other suitable antibacterial agents are described in U.S. Pat. No. 6,488,943.

7.3.1 Scalp Active Material

In an embodiment of the present invention, the personal care composition may comprise a scalp active material, which may be an anti-dandruff active. In an embodiment, the anti-dandruff active is selected from the group consisting of: pyridinethione salts; zinc carbonate; azoles, such as ketoconazole, econazole, and elubiol; selenium sulfide; particulate sulfur; keratolytic agents such as salicylic acid; and mixtures thereof. In a further embodiment, the anti-dandruff active may be an anti-dandruff particulate. In an embodiment, the anti-dandruff particulate is a pyridinethione salt. Such anti-dandruff particulate should be physically and chemically compatible with the components of the composition, and should not otherwise unduly impair product stability, aesthetics or performance.

Pyridinethione particulates are suitable particulate antidandruff actives for use in composition of the present invention. In an embodiment, the anti-dandruff active is a 1-hydroxy-2-pyridinethione salt and is in particulate form. In an embodiment, the concentration of pyridinethione anti-dandruff particulate ranges from about 0.01% to about 5%, by weight of the composition, or from about 0.1% to about 3%, or from about 0.1% to about 2%. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"; zinc pyrithione), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. Nos. 2,809,971; 3,236,733; 3,753, 196; 3,761,418; 4,345,080; 4,323,683; 4,379,753; and 4,470,982.

In an embodiment, in addition to the anti-dandruff active selected from polyvalent metal salts of pyrithione, the composition further comprises one or more anti-fungal and/or anti-microbial actives. In an embodiment, the anti-microbial active is selected from the group consisting of: coal tar, sulfur, charcoal, whitfield's ointment, castellani's paint, aluminum chloride, gentian violet, octopirox (piroctone olamine), ciclopirox olamine, undecylenic acid and its metal salts, potassium permanganate, selenium sulfide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. In an embodiment, the anti-microbial is selected from the group consisting of: itraconazole, ketoconazole, selenium sulfide, coal tar, and mixtures thereof.

In an embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the composition, the azole anti-microbial active is included in an amount of from about 0.01% to about 5%, or from about 0.1% to about 3%, or from about 0.3% to about 2%, by total weight of the composition. In an embodiment, the azole anti-microbial active is ketoconazole. In an embodiment, the sole anti-microbial active is ketoconazole.

The present invention may also comprise a combination of anti-microbial actives. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

In an embodiment, the composition comprises an effective amount of a zinc-containing layered material. In an embodiment, the composition comprises from about 0.001% to about 10%, or from about 0.01% to about 7%, or from about 0.1% to about 5% of a zinc-containing layered material, by total weight of the composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. In an embodiment, the ZLM is selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. In an embodiment, the ZLM is a layered double hydroxide conforming to the formula $[M^{2+}_{1-x}M^{3+}_x(OH)_2]^{x+}A^{m-}_{x/m} \cdot nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). In an embodiment, the ZLM is a hydroxy double salt conforming to the formula $[M^{2+}_{1-x}M^{2+}_{1+x}(OH)_{3(1-y)}]^+ A^{n-}_{(1=3y)/n} \cdot nH_2O$ where the two metal ions ($M^{2+}$) may be the same or different. If they are the same and represented by zinc, the formula simplifies to $[Zn_{1+x}(OH)_2]^{2+}2x\ A^- \cdot nH_2O$. This latter formula represents (where x=0.4) materials such as zinc hydroxychloride and zinc hydroxynitrate. In an embodiment, the ZLM is zinc hydroxychloride and/or zinc hydroxynitrate. These are related to hydrozincite as well wherein a divalent anion replace the monovalent anion. These materials can also be formed in situ in a composition or in or during a production process.

In an embodiment, the composition comprises basic zinc carbonate. Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA). Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

In embodiments having a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

7.3.2 Liquid Personal Care Compositions

Exemplary liquid rinse-off personal care compositions can include an aqueous carrier, which can be present at a level of from about 5% to about 95%, or from about 60% to about 85%. The aqueous carrier may comprise water, or a miscible mixture of water and organic solvent. Non-aqueous carrier materials can also be employed.

Such rinse-off personal care compositions can include one or more detersive surfactants. The detersive surfactant component can be included to provide cleaning performance to the product. The detersive surfactant component in turn comprises anionic detersive surfactant, zwitterionic or amphoteric detersive surfactant, or a combination thereof. A representative, non-limiting, list of anionic surfactants includes anionic detersive surfactant for use in the compositions can include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In one example, the anionic surfactant can be sodium lauryl sulfate or sodium laureth sulfate. The concentration of the anionic surfactant component in the product can be sufficient to provide a desired cleaning and/or lather performance, and generally ranges from about 2% to about 50%.

Amphoteric detersive surfactants suitable for use in the rinse-off personal care compositions are well known in the art, and include those surfactants broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438, 091, and products described in U.S. Pat. No. 2,528,378. Other examples of amphoteric surfactants can include sodium lauroamphoacetate, sodium cocoamphoactetate, disodium lauroamphoacetate disodium cocodiamphoacetate, and mixtures thereof. Amphoacetates and diamphoacetates can also be used.

Zwitterionic detersive surfactants suitable for use in the rinse-off personal care compositions are well known in the art, and include those surfactants broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants can include betaines, including cocoamidopropyl betaine.

The liquid rinse off personal care composition can comprise one or more phases. Such personal care compositions can include a cleansing phase and/or a benefit phase (i.e., a single- or multi-phase composition). Each of a cleansing phase or a benefit phase can include various components. The cleansing phase and the benefit phase can be blended, separate, or a combination thereof. The cleansing phase and the benefit phase can also be patterned (e.g. striped).

The cleansing phase of a personal care composition can include at least one surfactant. The cleansing phase can be an aqueous structured surfactant phase and constitute from about 5% to about 20%, by weight of the personal care composition. Such a structured surfactant phase can include sodium trideceth(n) sulfate, hereinafter STnS, wherein n can define average moles of ethoxylation. n can range, for example, from about 0 to about 3; from about 0.5 to about 2.7, from about 1.1 to about 2.5, from about 1.8 to about 2.2, or n can be about 2. When n can be less than 3, STnS can provide improved stability, improved compatibility of benefit agents within the personal care compositions, and increased mildness of the personal care compositions as disclosed in U.S. Pre-Grant Publication No. 2010/009285 A1.

The cleansing phase can also comprise at least one of an amphoteric surfactant and a zwitterionic surfactant. Suitable amphoteric or zwitterionic surfactants (in addition to those cited herein) can include, for example, those described in U.S. Pat. Nos. 5,104,646 and 5,106,609.

A cleansing phase can comprise a structuring system. A structuring system can comprise, optionally, a non-ionic emulsifier, optionally, from about 0.05% to about 5%, by weight of the personal care composition, of an associative polymer; and an electrolyte.

The personal care composition can optionally be free of sodium lauryl sulfate, hereinafter SLS, and can comprise at least a 70% lamellar structure. However, the cleansing phase could comprise at least one surfactant, wherein the at least one surfactant includes SLS. Suitable examples of SLS are described in U.S. Pre-Grant Publication No. 2010/0322878 A1.

Rinse-off personal care compositions can also include a benefit phase. The benefit phase can be hydrophobic and/or anhydrous. The benefit phase can also be substantially free of surfactant. A benefit phase can also include a benefit agent. In particular, a benefit phase can comprise from about 0.1% to about 50% benefit agent by weight of the personal care composition. The benefit phase can alternatively comprise less benefit agent, for example, from about 0.5% to about 20% benefit agent, by weight of the personal care composition. Examples of suitable benefit agents can include petrolatum, glyceryl monooleate, mineral oil, natural oils, and mixtures thereof. Additional examples of benefit agents can include water insoluble or hydrophobic benefit agents. Other suitable benefit agents are described in U.S. Pre-Grant Publication No. 2012/0009285 A1.

Non-limiting examples of glycerides suitable for use as hydrophobic skin benefit agents herein can include castor oil, safflower oil, corn oil, walnut oil, peanut oil, olive oil, cod liver oil, almond oil, avocado oil, palm oil, sesame oil, vegetable oils, sunflower seed oil, soybean oil, vegetable oil derivatives, coconut oil and derivatized coconut oil, cottonseed oil and derivatized cottonseed oil, jojoba oil, cocoa butter, and combinations thereof.

Non-limiting examples of alkyl esters suitable for use as hydrophobic skin benefit agents herein can include isopropyl esters of fatty acids and long chain esters of long chain (i.e. C10-C24) fatty acids, e.g., cetyl ricinoleate, non-limiting examples of which can include isopropyl palmitate, isopropyl myristate, cetyl riconoleate, and stearyl riconoleate. Other example can include hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of polyglycerin fatty acid esters suitable for use as hydrophobic skin benefit agents herein can include decaglyceryl distearate, decaglyceryl diisostearate, decaglyceryl monomyriate, decaglyceryl monolaurate, hexaglyceryl monooleate, and combinations thereof.

The rinse-off personal care composition can be applied by a variety of means, including by rubbing, wiping or dabbing with hands or fingers, or by means of an implement and/or delivery enhancement device. Non-limiting examples of implements include a sponge or sponge-tipped applicator, a mesh shower puff, a swab, a brush, a wipe (e.g., wash cloth), a loofah, and combinations thereof. Non-limiting examples of delivery enhancement devices include mechanical, electrical, ultrasonic and/or other energy devices. Employment of an implement or device can help delivery of the particulate antimicrobial agent to target regions, such as, for example, hair follicles and undulations that can exist in the underarm. The rinse-off care product can be sold together with such an implement or device. Alternatively, an implement or device can be sold separately but contain indicium to indicate usage with a rinse-off care product. Implements and delivery devices can employ replaceable portions (e.g., the skin interaction portions), which can be sold separately or sold together with the rinse-off care product in a kit.

7.3.3 Solid Personal Care Compositions

As noted herein, personal care compositions can take on numerous forms. One suitable form is that of a solid personal care composition. Solid compositions can take many forms like powder, pellets, bars, etc. These forms will generally be described herein as bar soap, but it should be understood that the solid composition could be in another form or shape. One example of a bar soap personal care composition can include from about 0.1% to about 35%, by weight of the personal care composition, of water, from about 45% to about 99%, by weight of the personal care composition, of soap, and from about 0.01% to about 5%, by weight of the personal care composition, of a particulate antimicrobial agent. Another suitable antimicrobial bar soap can include, for example, from about 0.1% to about 30%, by weight of the personal care composition, of water, from about 40% to about 99%, by weight of the personal care composition, of soap, and from about 0.25% to about 3%, by weight of the personal care composition, of a particulate antimicrobial agent.

Bar soap compositions can be referred to as conventional solid (i.e. non-flowing) bar soap compositions. Some bar soap composition can comprise convention soap, while others can contain synthetic surfactants, and still others can contain a mix of soap and synthetic surfactant. Bar compositions can include, for example, from about 0% to about 45% of a synthetic anionic surfactant. An example of a suitable conventional soap can include milled toilet bars that are unbuilt (i.e. include about 5% or less of a water-soluble surfactancy builder).

A personal care bar composition can include soap. By weight, the soap can be, for example, from about 45% to about 99%, or from about 50% to about 75%, by weight of the personal care composition. Such soaps can include a typical soap, i.e., an alkali metal or alkanol ammonium salt of an alkane- or alkene monocarboxylic acid. Sodium, magnesium, potassium, calcium, mono-, di- and tri-ethanol ammonium cations, or combinations thereof, can be suitable for a personal care composition. The soap included in a personal care composition can include sodium soaps or a combination of sodium soaps with from about 1% to about 25% ammonium, potassium, magnesium, calcium, or a mixture of these soaps. Additionally, the soap can be well-known alkali metal salts of alkanoic or alkenoic acids having from about 12 to about 22 carbon atoms or from about 12 to about 18 carbon atoms. Another suitable soap can be alkali metal carboxylates of alkyl or alkene hydrocarbons having from about 12 to about 22 carbon atoms. Additional suitable soap compositions are described in U.S. Pre-Grant Publication No. 2012/0219610 A1.

A personal care composition can also include soaps having a fatty acid. For example, one bar soap composition could contain from about 40% to about 95% of a soluble alkali metal soap of $C_8$-$C_{24}$ or $C_{10}$-$C_{20}$ fatty acids. The fatty acid can, for example, have a distribution of coconut oil that can provide a lower end of a broad molecular weight range or can have a fatty acid distribution of peanut or rapeseed oil, or their hydrogenated derivatives, which can provide an upper end of the broad molecular weight range. Other such compositions can include a fatty acid distribution of tallow and/or vegetable oil. The tallow can include fatty acid mixtures that can typically have an approximate carbon chain length distribution of 2.5% $C_{14}$, 29% $C_{16}$, 23% $C_{18}$, 2% palmitoleic, 41.5% oleic, and 3% linoleic. The tallow can also include other mixtures with a similar distribution, such as fatty acids derived from various animal tallows and/or lard. In one example, the tallow can also be hardened (i.e., hydrogenated) such that some or all unsaturated fatty acid moieties can be converted to saturated fatty acid moieties.

Suitable examples of vegetable oil include palm oil, coconut oil, palm kernel oil, palm oil stearine, soybean oil, and hydrogenated rice bran oil, or mixtures thereof, since such oils can be among more readily available fats. One example of a suitable coconut oil can include a proportion of fatty acids having at least 12 carbon atoms of about 85%. Such a proportion can be greater when mixtures of coconut oil and fats such as tallow, palm oil, or non-tropical nut oils or fats can be used where principle chain lengths can be $C_{16}$ and higher. The soap included in a personal care composition can be, for example, a sodium soap having a mixture of about 67-68% tallow, about 16-17% coconut oil, about 2% glycerin, and about 14% water.

Soap included in a personal care composition can also be unsaturated in accordance with commercially acceptable standards. For example, a soap included in a personal care composition can include from about 37% to about 45% unsaturated saponified material.

Soaps included in a personal care composition can be made, for example, by a classic kettle boiling process or modern continuous soap manufacturing processes wherein natural fats and oils such as tallow or coconut oil or their equivalents can be saponified with an alkali metal hydroxide using procedures well known to those skilled in the art. Soap can also be made by neutralizing fatty acids such as lauric ($C_{12}$), myristic ($C_{14}$), palmitic ($C_{16}$), or stearic ($C_{18}$) acids, with an alkali metal hydroxide or carbonate.

Soap included in a personal care composition could also be made by a continuous soap manufacturing process. The soap could be processed into soap noodles via a vacuum flash drying process. One example of a suitable soap noodle comprises about 67.2% tallow soap, about 16.8% coconut soap, about 2% glycerin, and about 14% water, by weight of the soap noodle. The soap noodles can then be utilized in a milling process to finalize a personal care composition.

EXAMPLES

The presently disclosed subject matter will be better understood by reference to the following Examples, which are provided as exemplary of the disclosure, and not by way of limitation.

Example 1: Accord A Containing Musk Compounds

This Example provides an accord comprising musk compounds. Table 1 provides a summary of the compounds and the amount of each compound used for Formulation A, which is a specific musk accord.

TABLE 1

| Formulation A composition | |
| --- | --- |
| Compound | % w/w |
| Musk T ® | 51.35 |
| Habanolide ® | 25 |
| Musk C14 ® | 15 |
| Exaltolide ® | 7 |
| Musk R1 ® | 0.15 |
| Raspberry Ketone @ 1% in dipropylene glycol | 1.5 |

Example 2: Accord B Containing Musk Compounds

This Example provides an accord comprising musk compounds. Table 2 provides a summary of the compound and the amount of each compound used for Formulation B, which is a specific musk accord.

TABLE 2

| Formulation B composition | |
| --- | --- |
| Compound | % w/w |
| Thesaron ® | 12.5 |
| Linalool | 37.5 |
| Linalyl acetate | 25 |
| Ambretone ® | 2.5 |
| Musk T ® | 22.5 |

Example 3: Accord C Containing Musk Compounds

This Example provides a fragrance accord comprising musk compounds. Table 3 provides a summary of the components that can be used for Formulation C, which is a specific musk accord.

TABLE 3

| Formulation C composition |
| --- |
| Compound |
| Linalool |
| Linalyl acetate |
| Habanolide ® |
| Ambretone ® |
| Musk T ® |

Example 4: Influence of Musk Compounds on Salivary Alpha-Amylase Levels

Salivary alpha-amylase is widely used as a biomarker for acute stress. The purpose of this study was to investigate the influence of individual fragrance compounds, particularly musk compounds, on a subject's salivary alpha-amylase levels before and after exposure to a stressor. The subject sniffed each musk compound, then was exposed to a stressor. The goal was to identify one or more specific musk compounds which caused the least amount of change in salivary alpha-amylase levels or decreased a subject's salivary alpha-amylase levels compared to before administration, thereby reducing or inhibiting a response to stress stimuli. The results are summarized in FIG. 1, which shows the percent change in salivary alpha-amylase levels after inhaling various fragrance compounds, as compared to the percent change in salivary alpha-amylase levels after inhaling a control (dipropylene glycol). The p values of the control as compared to each musk compound were calculated as follows: rosamusk (p=0.0366), habanolide (p=0.1163), ambrettolide (p=0.1397).

Example 5: Influence of Musk Compounds on Salivary Cortisol Levels

Figure 2:
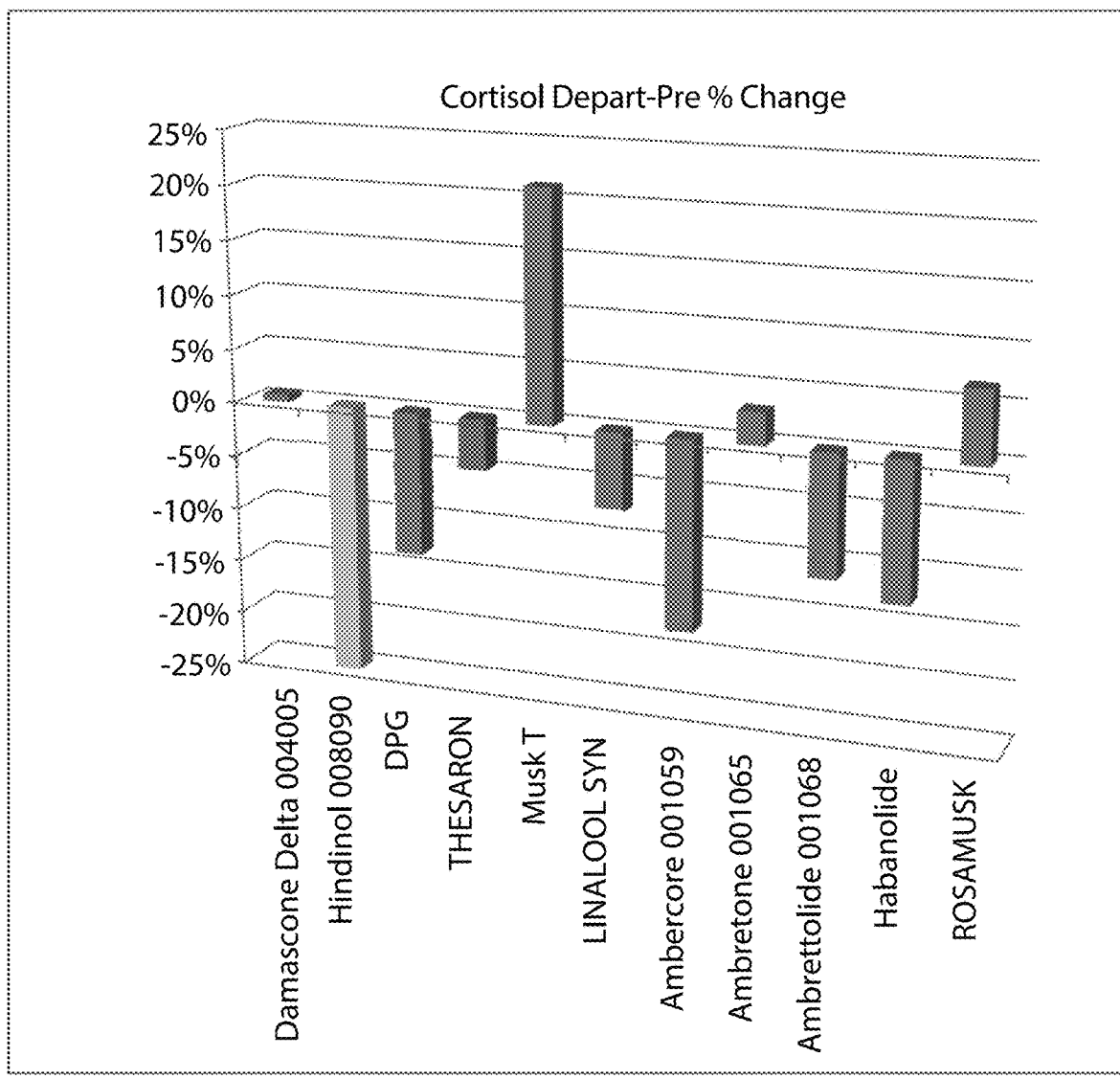
FIG. 2 provides a graphical analysis of a subject's levels of salivary cortisol, measured before and after exposure to a stressor. In the graphic, each compound tested is provided (x-axis), and the change in salivary cortisol, measured before and after exposure to a stressor, is evaluated on a percent scale (y-axis).

Salivary cortisol is widely used as a biomarker for stress. The purpose of this study was to investigate the influence of individual fragrance compounds, particularly musk compounds, on a subject's cortisol levels before and after exposure to a stressor. The subject sniffed each musk compound, then was exposed to a stressor. The goal was to identify one or more specific musk compounds which caused the least amount of change in cortisol levels or decreased a subject's cortisol levels compared to before administration, thereby reducing or inhibiting a response to stress stimuli. The results are summarized in FIG. 2, which shows the percent change in salivary cortisol levels after inhaling various fragrance compounds, as compared to the percent change in salivary cortisol levels after inhaling a control (dipropylene glycol).

Example 6: Influence of Macrocyclic Musk Compounds on Salivary Alpha-Amylase Levels This Example evaluated the effects of several macrocylic musk compounds on salivary alpha-amylase levels of a test group.

Twelve to fourteen female panelists age 30-45 participated in this study for each of the test materials. Stress was induced using a timed ten minute mathematical/word test in a small group competition setting. The musk material was introduced at intervals during the stress test.

Saliva was collected before and immediately after the stress test. Saliva samples were assayed for salivary alpha-amylase activity using a commercially available kinetic reaction assay kit (Salimetrics®, State College, Pa.).

The change in a panelist's salivary alpha-amylase level for each tested musk compound is summarized in Table 4.

TABLE 4

Summary of salivary alpha-amylase level for each tested musk compound.

| Musk Compound | Percent change in salivary alpha-amylase |
| --- | --- |
| Solvent only (control) | 66.8% |
| Musk T ® | 47.1% |
| Ambretone ® | 36.9% |
| Ambrettolide ® (9Z)-17-oxacycloheptadec-6-en-1-one | 13.1% |

TABLE 4-continued

Summary of salivary alpha-amylase level for each tested musk compound.

| Musk Compound | Percent change in salivary alpha-amylase |
| --- | --- |
| Habanolide ® (12E)-1-oxacyclohexadec-(12-en-2-one | 4.7% |

Results in Table 4 show that salivary alpha-amylase levels in the control sample increased by nearly 67%. However, the data shows that the use of these individual macrocyclic musk compounds resulted in substantially lower salivary alpha-amylase levels after the stress test. Therefore, the data demonstrated that the inhalation of these macrocyclic musk compounds inhibited the increase of salivary alpha-amylase under stress.

Example 7: Influence of Non-Macrocyclic Musk Compounds on Salivary Alpha-Amylase Levels This Example evaluated the effects of two non-macrocyclic musk compounds on salivary alpha-amylase levels of a test group.

Materials and methods were the same as Example 6. The change in a panelist's salivary alpha-amylase level for each tested musk compound is summarized in Table 5.

TABLE 5

Summary of salivary alpha-amylase level for each tested musk compound.

| Musk Compound | Percent change in salivary alpha-amylase |
| --- | --- |
| Solvent only (control) | 66.8% |
| Hindinol ® (E)-2-methyl-4-(2,2,3-trimethyl-1-cyclopent-3-enyl)but-2-en-1-ol | 82.3% |
| ethyl (1R,6S)-2,2,6-trimethylcyclohexane-1-carboxylate | 70.7% |

Results in Table 5 show that salivary alpha-amylase levels for two specific non-macrocyclic musk compounds increased as much as or more than the control solvent. Therefore, inhalation of these two non-macrocyclic musk compounds individually did not inhibit the increase of salivary alpha-amylase under stress.

Example 8: The Influence of Musk Compound Musk T on Salivary Alpha-Amylase and Cortisol Reactivity to Acute Stress Fourteen female panelists age 30-45 participated in this study. Stress was induced using a timed ten minute mathematical/word test in a small group competition setting. Fragrance was introduced at intervals during the stress test. Saliva was collected before (Pre) and immediately after (Post) the stress test. Saliva samples were assayed for salivary alpha-amylase using a commercially available kinetic reaction assay kit and for salivary cortisol using a highly sensitive enzyme immunoassay kit (Salimetrics®, State College, Pa.).

The Musk T compound was formulated in a fragrance at an amount of 2.5% by weight for use in the present example. 75% by weight of a floral fragrance was admixed with 25% by weight Musk T to form an admixture. 10% of the admixture was then diluted with 90% DPG to form a musk containing fragrance.

Figure 3:
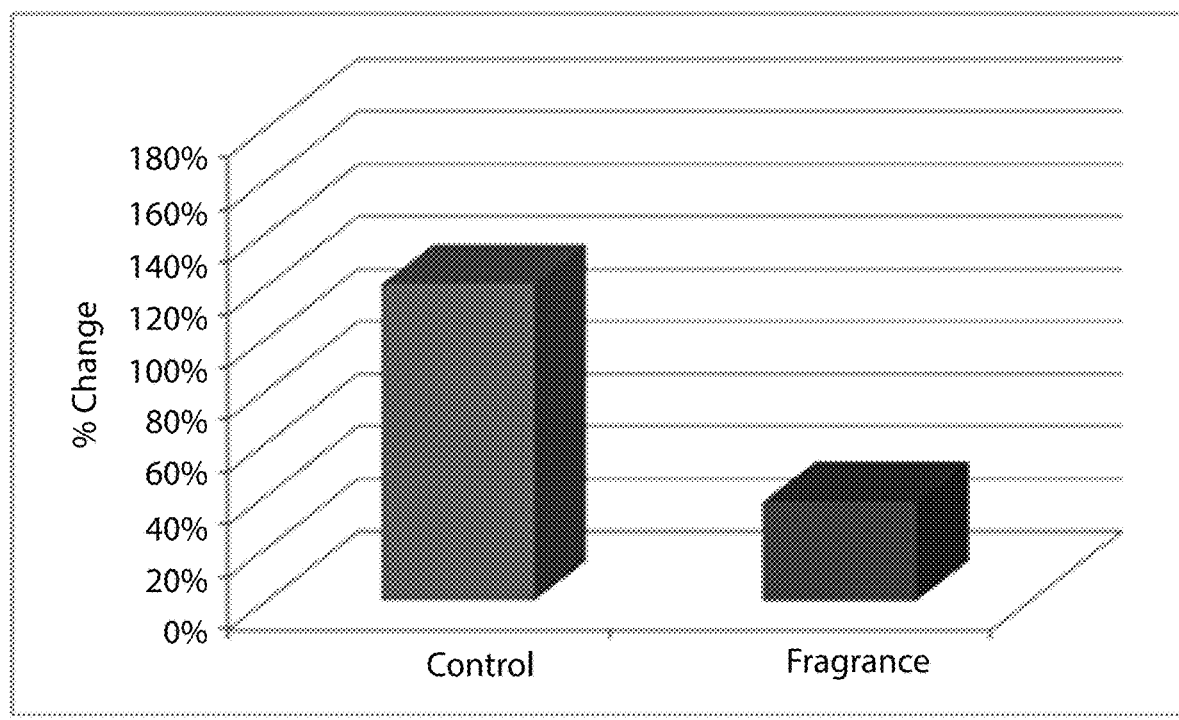
FIG. 3 shows the average percentage change in salivary alpha-amylase (sAA) in response to a stress test, in the presence of a musk containing fragrance, as described by Example 8.

As shown in FIG. 3, Pre vs. Post salivary alpha-amylase level increased in response to the stress test, 38% with fragrance and 120% with DPG alone.

Figure 4:
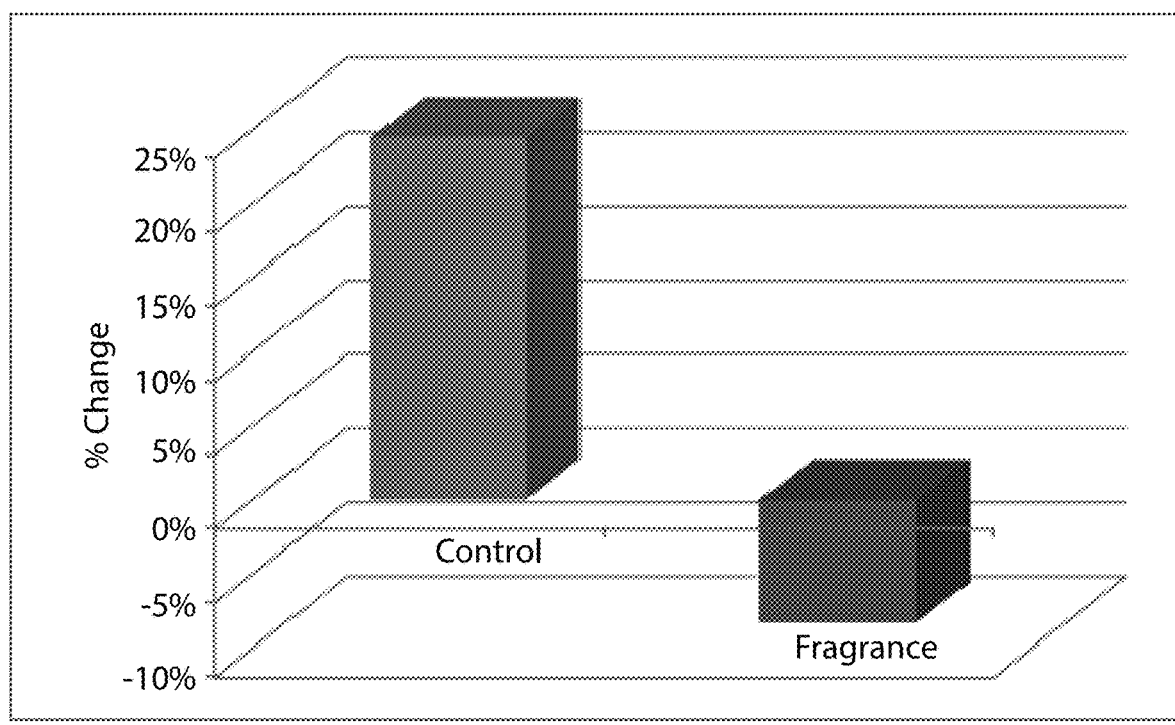
FIG. 4 shows the average percentage change in salivary cortisol in response to a stress test, in the presence of a musk containing fragrance, as described by Example 8.

As shown in FIG. 4, Pre vs. Post salivary cortisol level in response to the stress test decreased 8% with fragrance and increased 24% with DPG alone.

The increase of salivary alpha-amylase during the stress test in the presence of the Musk T compound was less than the control. With regard to changes in cortisol during the stress test, in the presence of Musk T, there was a decrease in cortisol levels, which is in contrast to the increase observed for the control. The results of this study demonstrate that the presence of Musk T during a stress task has a positive influence by blunting the effect of the stressor and that both the sympathetic and the HPA axis may be involved.

Example 9: The Influence of Musk Compound Musk T on Brain Wave Function and Salivary Alpha-Amylase and Cortisol Reactivity to Acute Stress This study was conducted using the methods as described above for Example 8. The Musk T compound was formulated in an amount of 10% by weight in DPG for use as a musk containing fragrance in the present example.

Contingent Negative Variant (CNV) analysis was conducted on brain waves recorded from subjects using EEG (electroencephalography) in the presence of the musk fragrance compound. CNV analysis is summarized in Okazaki et al., Proceedings of the 13th International Congress of Flavours, Fragrances and Essential Oils, 15-19 Oct. 1995.

Figure 5:
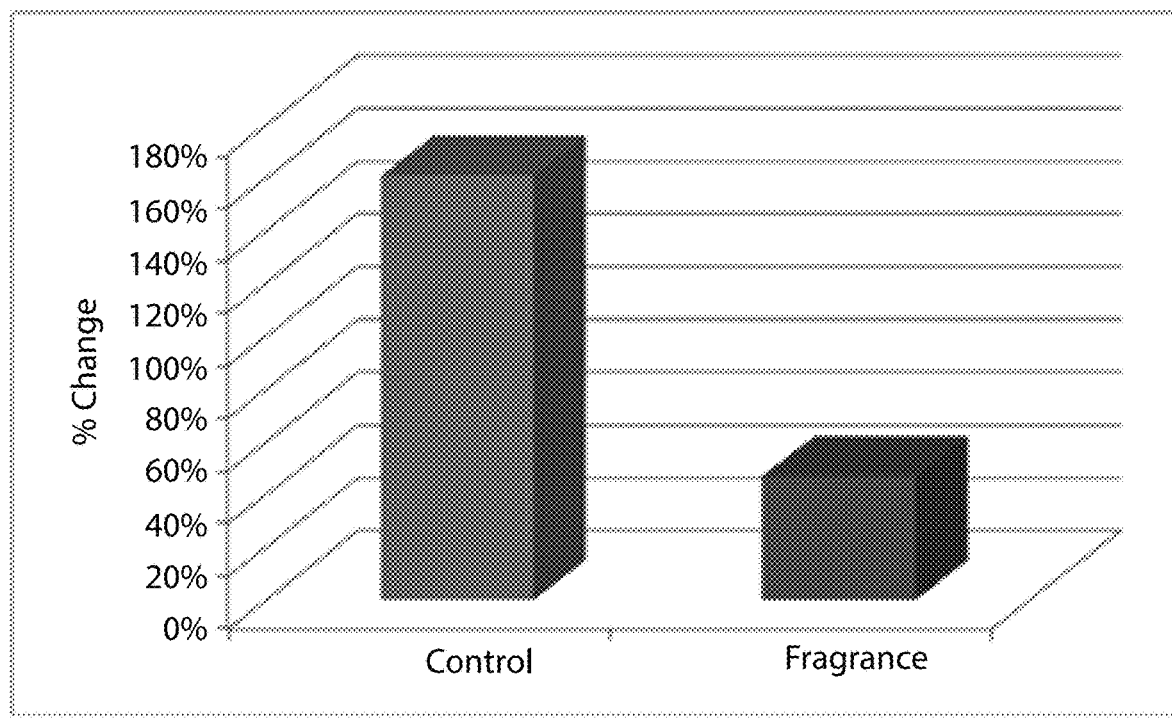
FIG. 5 shows the average percentage change in sAA in response to a stress test, in the presence of a musk containing fragrance, as described by Example 9.

As shown in FIG. 5, Pre vs. Post salivary alpha-amylase level increased in response to the stress test, 47% with fragrance and 161% with DPG alone.

Figure 6:
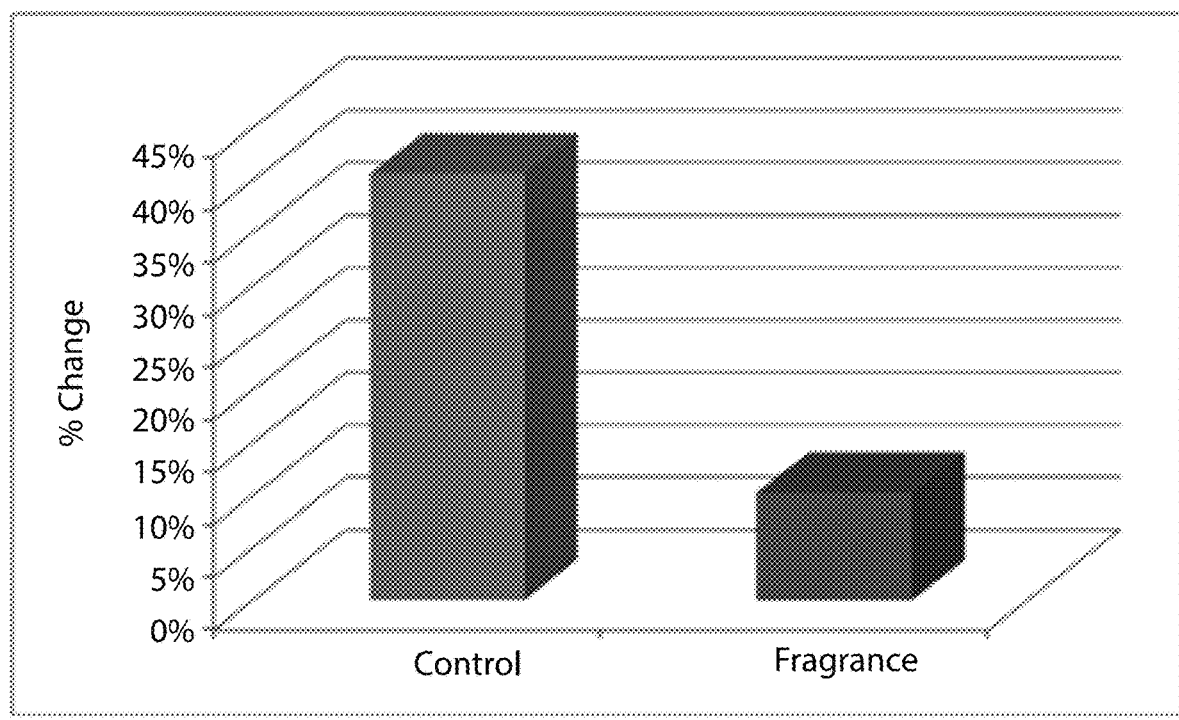
FIG. 6 shows the average percentage change in salivary cortisol in response to a stress test, in the presence of a musk containing fragrance, as described by Example 9.

As shown in FIG. 6, Pre vs. Post salivary cortisol level increased in response to the stress test, 10% with fragrance and 41% with DPG alone.

Contingent Negative Variant (CNV) analysis of brain waves in subjects exposed to the fragrance shows a 32.5% increase in the level of relaxation when exposed to the fragrance.

The increase of salivary alpha-amylase during the stress test in the presence of Musk T was less than the control. Similarly, the increase in cortisol levels during the stress test was lower in the presence of Musk T than control. Furthermore, CNV analysis of EEG data from subjects exposed to Musk T identified an increase in brain waves associated with an emotional state of relaxation. The results of this study demonstrate that the presence of a Musk T fragrance during a stress task has a positive influence by blunting the effect of the stressor and that both the sympathetic and the HPA axis may be involved.

Example 10: The Influence of Rosamusk on Salivary Alpha-Amylase and Cortisol Reactivity to Acute Stress The study was conducted using the methods as described above for Example 8. The Rosamusk compound was formulated in an amount of 10% by weight in DPG for use as a musk containing fragrance in the present example.

Figure 7:
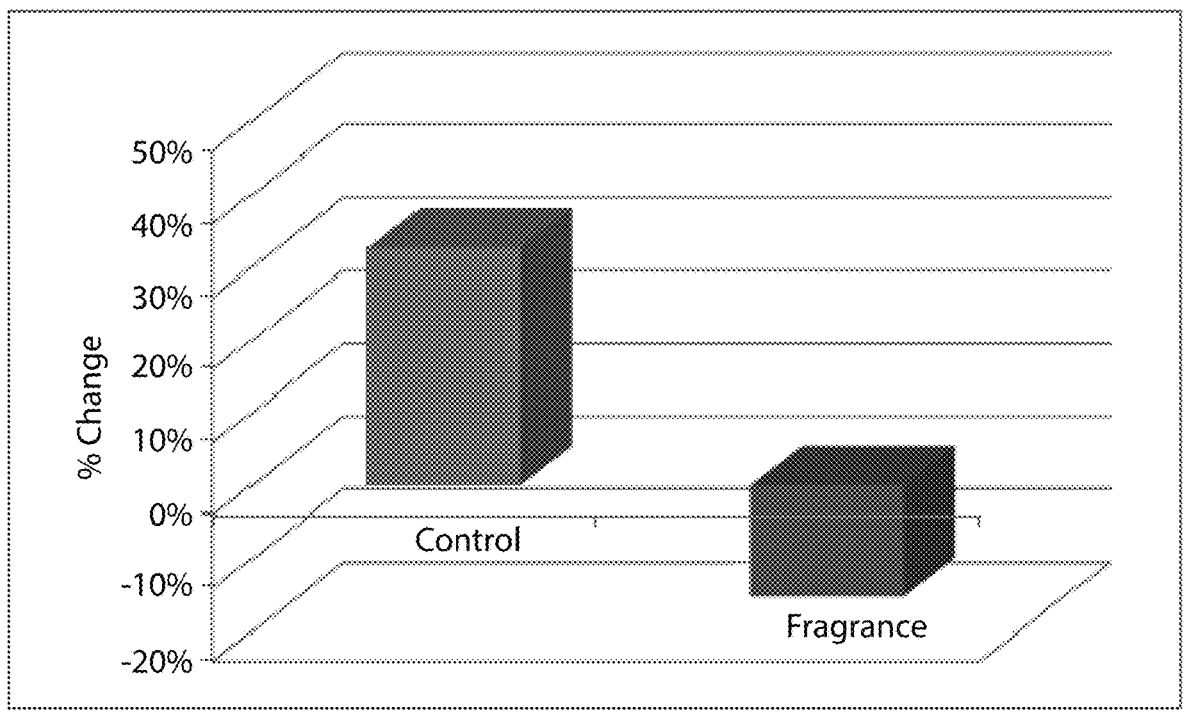
FIG. 7 shows the average percentage change in sAA in response to a stress test, in the presence of a musk containing fragrance, as described by Example 10.

As shown in FIG. 7, Pre vs. Post salivary alpha-amylase level in response to the stress test decreased 15% with fragrance and increased 33% with DPG alone.

Figure 8:
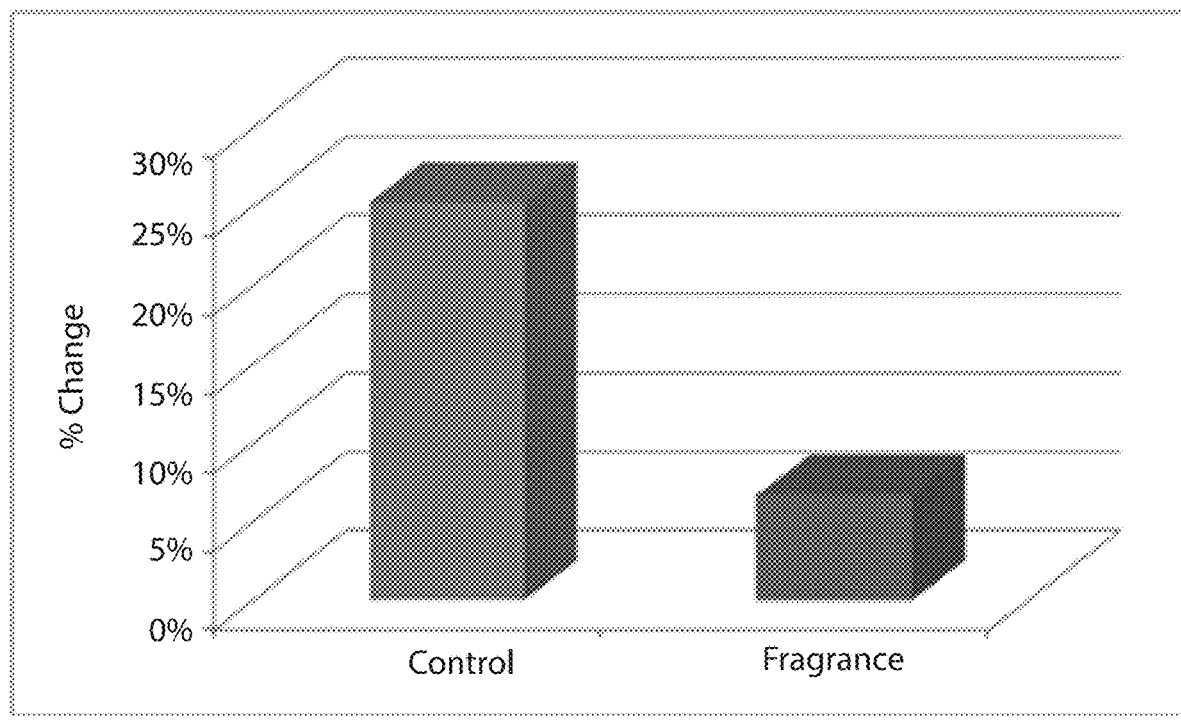
FIG. 8 shows the average percentage change in salivary cortisol in response to a stress test, in the presence of a musk containing fragrance, as described by Example 10.

As shown in FIG. 8, Pre vs. Post salivary cortisol level increased in response to the stress test, 7% with fragrance and 25% with DPG alone.

During the stress test, the level of salivary alpha-amylase in the presence of Rosamusk decreased, while the level of salivary alpha-amylase increased for the control. With regard to changes in cortisol during the stress test, the increase in cortisol level during the stress test was lower in the presence of Rosamusk than control. The results of this study demonstrate that the presence of Rosamusk during a stress task has a positive influence by blunting the effect of the stressor and that both the sympathetic and the HPA axis may be involved.

Example 11: The Influence of Musk Compound Musk T on Salivary Alpha-Amylase and Cortisol Reactivity to Acute Stress and Consumer Self-Report Assay of Emotional State The study was conducted using the methods as described above for Example 8.

In the present example, 54% by weight of a floral fragrance was admixed with 46% by weight Musk T to form an admixture. 10% of the admixture was then diluted with 90% by weight DPG to form the musk containing fragrance. Therefore, the Musk T compound was prepared in an amount of 4.6% by weight in the overall fragrance composition.

In addition to measuring salivary alpha-amylase level and cortisol level before and after the stress test in the presence or absence of a musk fragrance compound, a panel of consumers (N=15) provided a consumer self-report regarding their emotional state after exposure to the fragrance. The panelists also conducted a self-reported measurement of emotion, as determined by a PANAS (Positive Affect Negative Affect Scale) questionnaire.

Figure 9:
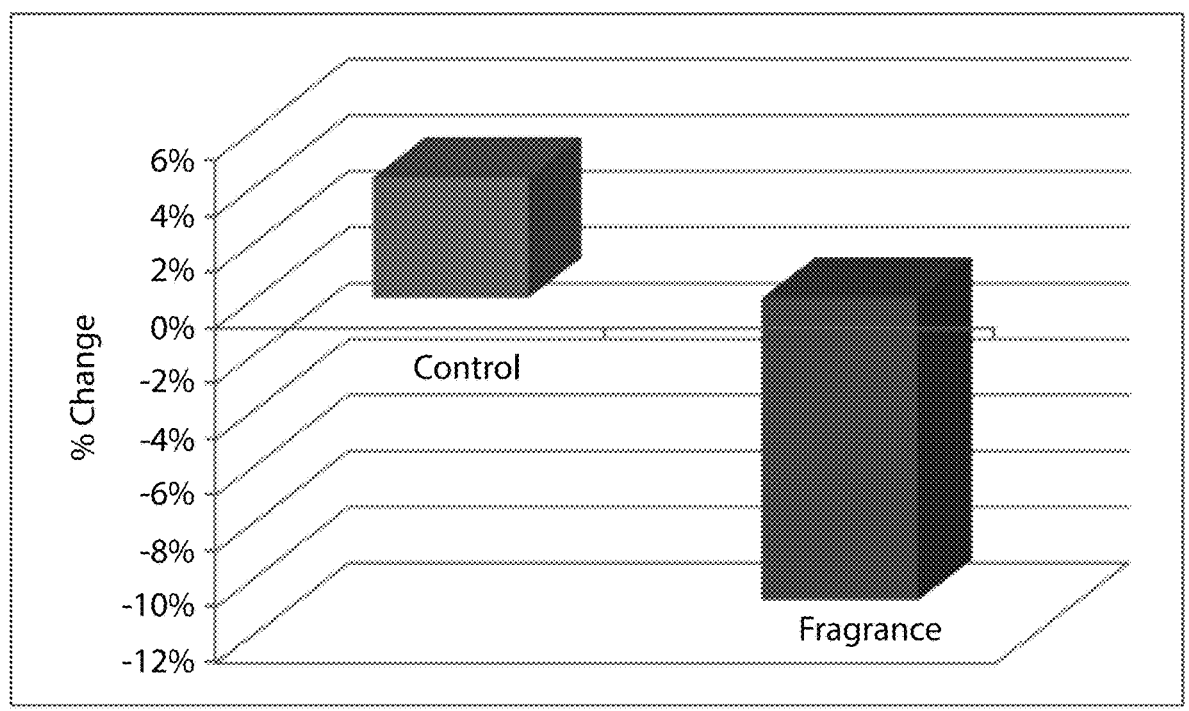
FIG. 9 shows the average percentage change in sAA in response to a stress test in the presence of a musk containing fragrance, as described by Example 11.

As shown in FIG. 9, Pre vs. Post salivary cortisol level in response to the stress test decreased 11% with fragrance and increased 4% with DPG alone.

The Pre vs. Post salivary alpha-amylase level in response to the stress test increase 35.3% with fragrance and increased 50.8% with DPG alone.

In the consumer self-report questionnaire, 100% of panelists felt "at ease," "relaxed" and "calm" after exposure to the fragrance.

With regard to the consumer self-report PANAS assay, there was a decrease of 6.4% in stimulating attributes after exposure to the fragrance.

With regard to changes in salivary alpha-amylase before and after the stress test, in the presence of the Musk T fragrance, there was an increase in salivary alpha-amylase levels. However, the increase of the control (DPG alone) was much higher than that with the Musk T fragrance (35.3% compared to 50.8% DPG alone).

Similarly, according to the consumer report questionnaires, the Musk T fragrance resulted in emotional states of relaxation, with a decrease in stimulating attributes. The results of this study demonstrate that the presence of the Musk T fragrance during a stress task has a positive influence by blunting the effect of the stressor and that both the sympathetic and the HPA axis may be involved.

Example 12: The Influence of Formulation B on Salivary Alpha-Amylase and Salivary Cortisol Levels This study was conducted using Formulation B as described above for Example 2. A fragrance composition was prepared using 10% w/w of Formulation B admixed with 90% w/w of a fruity fragrance composition. Salivary samples were taken before and after a stress test.

Figure 10:
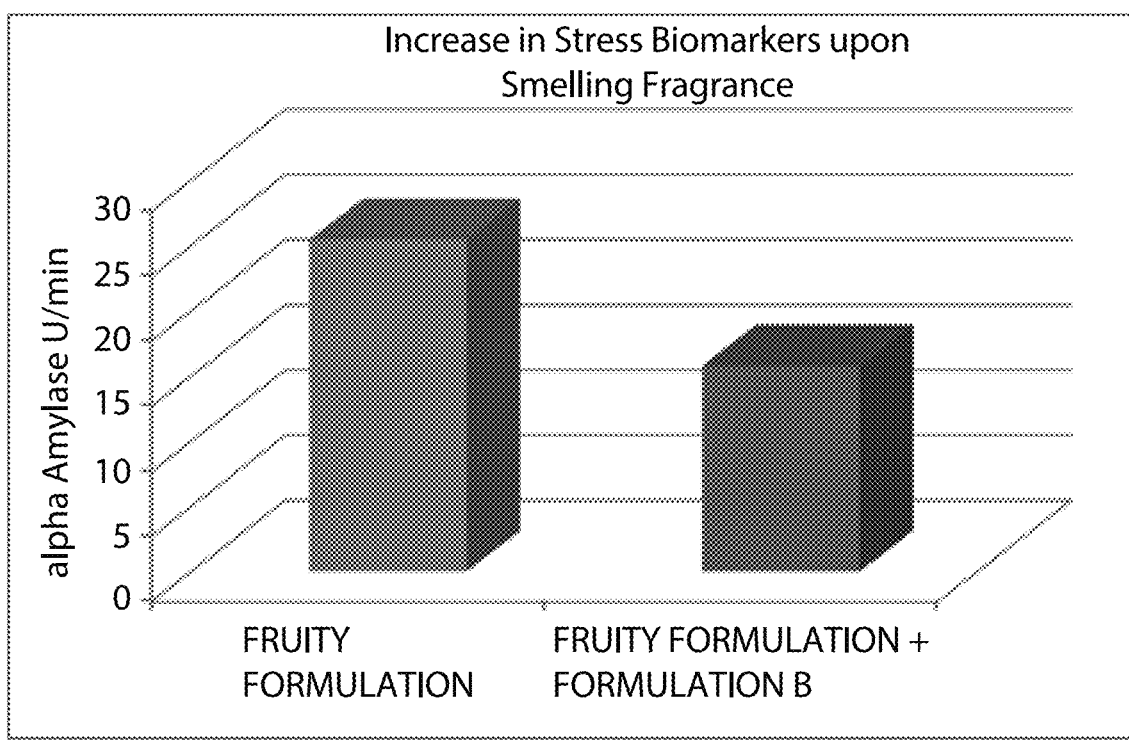
FIG. 10 shows the levels of salivary alpha-amylase produced in response to a stress test, in the presence of the combination of Formulation B and the fruity fragrance composition versus the fruity fragrance composition alone, as described in Example 12.

As shown in FIG. 10, salivary alpha-amylase levels were lower in response to the combination of Formulation B and the fruity fragrance composition versus the fruity fragrance composition alone.

Figure 11:
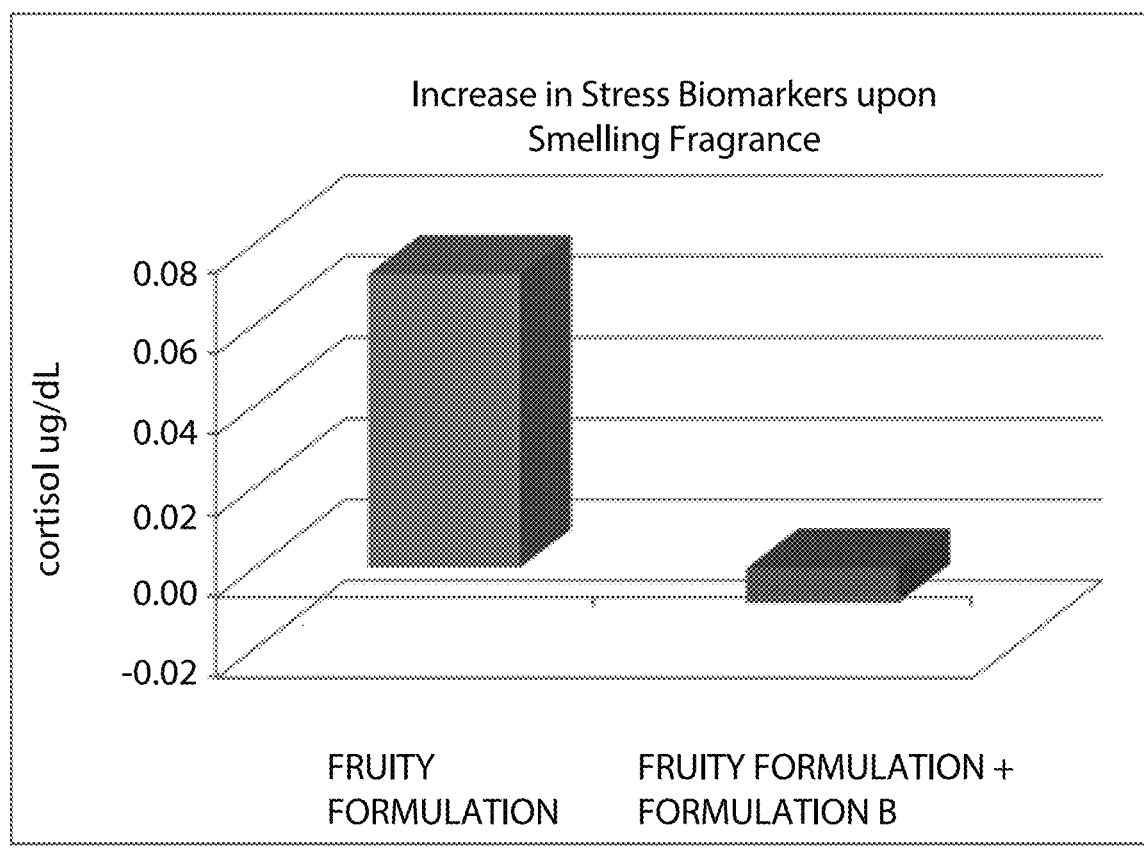
FIG. 11 shows the levels of salivary cortisol produced in response to a stress test, in the presence of the combination of Formulation B and the fruity fragrance composition versus the fruity fragrance composition alone, as described in Example 12.

As shown in FIG. 11, salivary cortisol levels were lower in response to the combination of Formulation B and the fruity fragrance composition versus the fruity fragrance composition alone.

Figure 12:
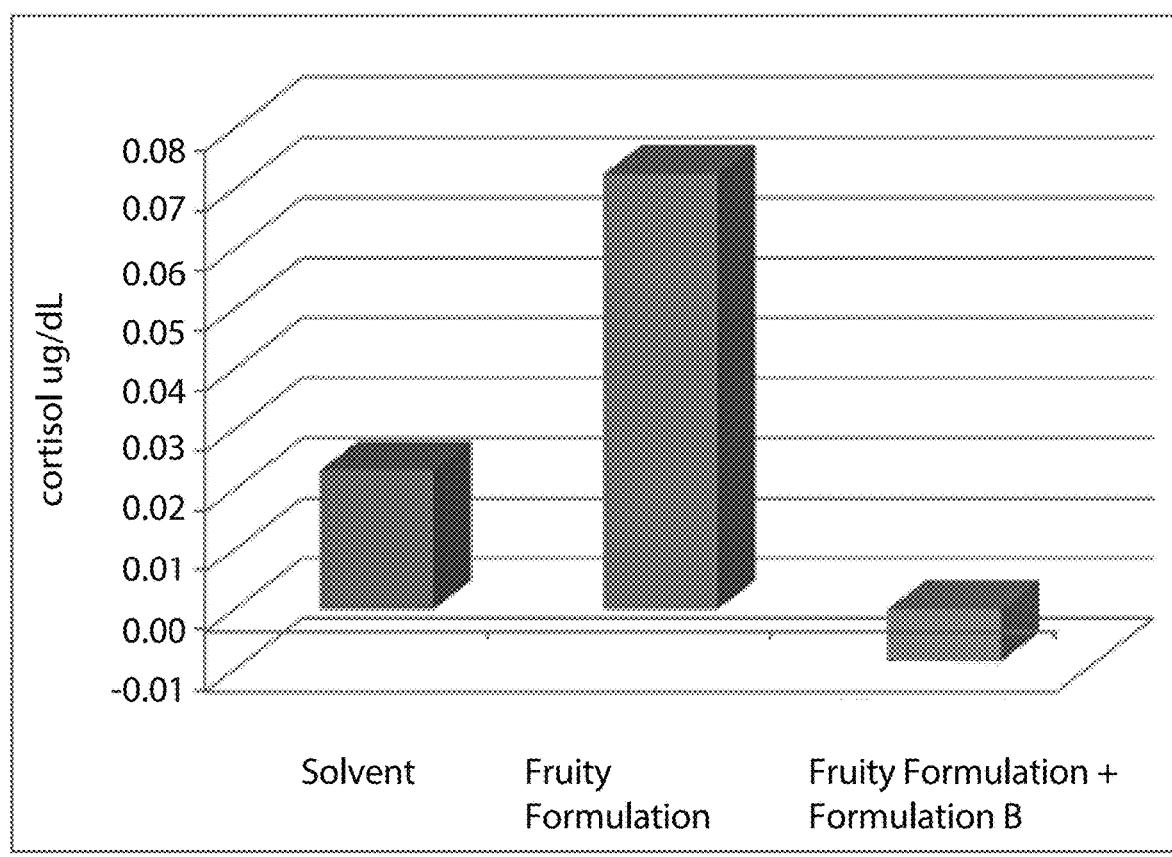
FIG. 12 shows the levels of salivary cortisol produced in response to a stress test in the presence of the combination of Formulation B and the fruity fragrance composition versus the fruity fragrance composition alone and versus solvent alone, as described in Example 12.

As shown in FIG. 12, salivary cortisol levels were lower in response to the combination of Formulation B and the fruity fragrance composition versus the fruity fragrance composition alone and versus solvent alone.

The results of this study demonstrate that both salivary alpha-amylase and salivary cortisol levels decrease in the presence of Formulation B in combination with the fruity fragrance composition more than in the presence of the fruity fragrance composition alone. Therefore, the data demonstrated that the combination of Formulation B and the fruity fragrance composition inhibited the increase of salivary alpha-amylase and salivary cortisol under stress.

Example 13: Compounds Effective Against Stressors

The present Example provides the results of those compounds that demonstrated a change in salivary amylase levels, cortisol levels, or both. Dipropylene glycol (DPG) was used as the solvent and control.

Stress was induced in a number of panelists (about 10-15) for each tested compound using a timed ten minute mathematical/word test in a small group competition setting. The test compound was introduced at intervals during the stress test.

Saliva was collected before and immediately after the stress test. Saliva samples were assayed for salivary cortisol levels and salivary alpha-amylase activity using a commercially available kinetic reaction assay kit (Salimetrics®, State College, Pa.).

The change in a panelist's salivary alpha-amylase and salivary cortisol levels for each tested compound is summarized in Table 6.

TABLE 6

| Compound | Salivary Amylase Data | Cortisol Data |
| --- | --- | --- |
| Ambrettolide | +13.16% <br> p = 0.1492 vs <br> DPG = +60.7% | −11.25% <br> p = 0.7782 vs <br> DPG = −10.9% |
| Habanolide | +4.67% <br> p = 0.1382 vs <br> DPG = +60.7% | −20.6% <br> p = 0.4808 vs <br> DPG = −10.9% |
| L-Muscone | +14.5% <br> P = 0.3275vs <br> DPG = +60.7% | +25.6% <br> P = 0.0175 <br> DPG = −10.9% |
| Phantolide | −19.2% <br> p = 0.0053 vs <br> DPG = +60.7% | −12.3% <br> p = 0.9633 vs <br> DPG = −10.9% |
| Rosamusk | −15.2% <br> p = 0.0605 vs <br> DPG = +60.7% | +6.68% <br> p = 0.2048 vs <br> DPG = −10.9% |
| Hindinol | +82.3% <br> p = 0.9514 vs <br> DPG = +60.7% | −25.0% <br> p = 0.0644 vs <br> DPG = −10.9% |
| 3-methyl-5-((1R)-2,2,3-trimethylcyclopentyl)pentan-2-one | −6.1% <br> p = 0.0378 vs <br> DPG = +60.7% | −16.5% <br> p = 0.765 vs <br> DPG = −10.9% |

The results of this study demonstrated that salivary alpha-amylase and salivary cortisol levels decrease in the presence of rosamusk, Habanolid® ((12E)-1-oxacyclohexadec-12-en-2-one), ambrettolide (17-oxacycloheptadec-6-en-1-one), Muscone L, 3-methyl-5-((1R)-2,2,3-trimethylcyclopentyl)pentan-2-one, phantolide (1-(1,1,2,3,3,6-hexamethyl-2H-inden-5-yl)ethanone) more than in the presence of DPG alone. Salivary cortisol levels decreased in the presence of Hindinol® ((E)-2-methyl-4-(2,2,3-trimethyl-1-cyclopent-3-enyl)but-2-en-1-ol) more than in the presence of DPG alone.

Example 14: The Influence of Formulation A on Salivary Alpha-Amylase and Salivary Cortisol Levels This study was conducted using Formulation A as described above for Example 1. A fragrance composition was prepared using 10% w/w of Formulation A admixed with 90% w/w of a fragrance composition. Salivary samples were taken before and after a stress test to evaluate alpha-amylase and cortisol inhibition. The participants were exposed to Formulation A in the fragrance composition at different time points including, before application of the stressor, during the duration of the stressor and during only the first half of exposure to the stressor. The sniff time points and results are summarized in Table 7.

TABLE 7

Summary of alpha-amylase and cortisol inhibition before and during a stress test.

| Event | Percent change in alpha amylase | Percent change in cortisol |
| --- | --- | --- |
| Solvent only (control) | 13.21% | 22.24% |
| 10 sniffs during stressor (normal procedure) | 42.56% | −10.36% |
| Sniff only 5 times during first half of stressor | 54.06% | −3.52% |
| Sniff only before stressor | −26.08% | 1.55% |

The results of this study demonstrate that cortisol levels decreased in the presence of Formulation A in combination with fragrance composition more than in the presence of solvent alone. Therefore, the data demonstrated that the combination of Formulation A and fragrance composition inhibited the increase of salivary alpha-amylase under stress when smelled before application of the stressor.

Example 15: Dose Response Data of Formulation A

In this Example, Formulation A from Example 1 was tested at different amounts (based on drops) to determine the dose response of percent change in a subject's salivary alpha-amylase and salivary cortisol levels.

Methodology for number of drops. Ten to twenty-four panelists age 30-45 participated in this study. The amount of fragrance tested was divided equally and applied onto 6 blotter cards each 3 by 5 inches in size. They were weighed and placed in the test room 30 minutes before the stress test to equilibrate.

Stress was induced using a timed ten-minute mathematical/word test in a small group competition setting. The blotter cards were removed and weighed again after the stress test. The difference in weight represented the weight loss in the 3,630 cubic feet test room.

Saliva was collected before (Pre) and immediately after (Post) the stress test. Saliva samples were assayed for salivary alpha-amylase using a commercially available kinetic reaction assay kit and for salivary cortisol using a highly sensitive enzyme immunoassay kit (Salimetrics®, State College, Pa.).

The concentration of the formulation in the headspace was determined. The concentration of the mixture in the headspace was measured and the weight loss of the mixture at the end of the test was calculated. The data summary is provided below.

TABLE 8

Summary of Dose Response Data for 60 drops of mixture

| Concentration of mixture in air (ug/cf) | Concentration of Formulation A (ng/cf) | Percent change in alpha-amylase | Percent change cortisol |
|---|---|---|---|
| 0 (No drops) | 0 | 49.6% | 7.8% |
| 36 ug/cf (60 drops mixture) | 12 ng/cf | 23.4% | −4.5% |

Example 16: Dose Response Data of Formulation A

In this Example, Formulation A from Example 1 was tested at different amounts (based on drops) using the procedure described in Example 15. The data summary is provided below.

TABLE 9

Summary of Dose Response Data for various drops of mixture

| Concentration of mixture in air (ug/cf) | Concentration of Formulation A (ng/cf) | Percent change in alpha-amylase | Percent change cortisol |
|---|---|---|---|
| 1.3 ug/cf (6 drops mixture) | 0.4 ng/cf | 62.7% | 16.0% |
| 20 ug/cf (12 drops mixture) | 6.7 ng/cf | 65.0% | 31.9% |
| 22 ug/cf (18 drops mixture) | 7.4 ng/cf | 6.1% | −0.1% |

Example 17: Dose Response Data of Formulation A

In this Example, Formulation A from Example 1 was tested at different amounts (based on drops) using the procedure described in Example 15. The data summary is provided below.

TABLE 10

Summary of Dose Response Data

| Concentration of mixture in air (ug/cf) | Concentration of Formulation A (ng/cf) | Percent change in alpha-amylase | Percent change cortisol |
|---|---|---|---|
| 44 ug/cf (36 drops mixture) | 14.6 ng/cf | 35.0% | 14.8% |
| 83 ug/cf (90 drops mixture) | 27.7 ng/cf | 35.8% | −5.0% |
| 99.5 ug/cf (120 drops mixture) | 33.17 ng/cf | 31.6% | 20.2% |

Example 18: Consumer Products and Method for Determining Concentrations

Formulation A, as shown in Examples 15-17, in the vapor phase at 7.4 ng/ft$^3$ to 27.7 ng/ft$^3$ provides a reduction of cortisol and alpha amylase markers. This indicates stress reduction in a subject.

The concentration in shampoo and APDO soft solid product that such accord should be added to arrive at a vapor phase of 7.4 ng/ft$^3$ to 27.7 ng/ft$^3$ is provided below. This procedure can be used to determine the in product concentration required for consumer products.

Estimation Method:

The chassis-air partition coefficient can be measured for materials in various chassis.

$$K_{i,chassis-air} = \frac{C_{i,chassis}}{C_{i,air}} \quad (1)$$

where:

$K_{i,chassis-air}$ is the chassis-air partition coefficient for component i in the fragrance formula $C_{i,\,chassis}$ is the concentration of component i in the product formula chassis in molarity, M $C_{i,\,air}$ is the concentration of component i in the headspace air in equilibrium with the formula chassis in molarity, M For the "Example Accord" in the BC-162 shampoo chassis components, the log chassis-air partition coefficients are as listed in Table 11.

TABLE 11

Air Partition Coefficients

| CAS | Name | logK, BC162 | logK, APDO Soft Solid |
|---|---|---|---|
| 25265-71-8 | DIPROPYLENE GLYCOL | 5.860 | 4.305 |
| 5471-51-2 | PARA HYDROXY PHENYL BUTANONE | 7.809 | 6.135 |
| 106-02-5 | EXALTOLIDE | 5.356 | 6.729 |
| 111879-80-2 | HABANOLIDE | 5.505 | 6.693 |
| 3391-83-1 | MUSK RI | 5.780 | 6.970 |
| 54982-83-1 | ZENOLIDE | 6.131 | 6.966 |
| 105-95-3 | ETHYLENE BRASSYLATE | 6.345 | 7.306 |

The following is a conversion to get to units of molarity in air:

$$C_{i,air}\,\frac{mol}{L} = C_{i,air}\,\frac{ng}{ft^3} \cdot \left(\frac{ft^3}{28.317\,L}\right) \cdot \left(\frac{1\,g}{10^p\,ng}\right) \cdot \left(\frac{mol}{MW \cdot g}\right) \quad (2)$$

To determine the concentration in chassis, $C_{i,chassis}$, the following calculation is used:

$$C_{i,chassis}\,\frac{mol}{L} = C_{i,air}\,\frac{mol}{L} \cdot 10^{\log K} \quad (3)$$

Weight percent in the chassis is determined by the following:

$$w_i = C_{i,chassis} \cdot \frac{mol_i}{L_{chassis}} \cdot \frac{MW_i \frac{g_i}{mol_i}}{\rho_{chassis} \frac{g_{chassis}}{mL_{chassis}} \cdot 1000 \frac{mL}{L}} \quad (4)$$

where:

$\rho_{chassis}$ is the density of the chassis in g/mL
$MW_i$ is the molecular weight of component i
Weight percent of the individual components of the accord are summed to generate the total weight percent to be used in the chassis.

$$w_{accordiotal\ chassis} = \sum_i w_i \quad (5)$$

Target weight percents for total Example Accord in product are as shown in Table 12.

TABLE 12

| Target Weight Percents | | |
|---|---|---|
| Headspace, ng/cf | 7.4 | 27.7 |
| Chassis | Low | High |
| Shampoo | 0.000017% | 0.000064% |
| Soft Solid Antiperspirant | 0.000018% | 0.000067% |

The above numbers assume equilibrium headspace of the neat product.

When a consumer product is used, often the touchpoint that the consumer experiences will require a higher level in the product such that when fragrance is lost through a wash process or diluted in the surrounding air, the concentration is still within the limits.

When in use conditions are considered, the calculated neat product concentration should be increased by a factor of from about three orders of magnitude to about five orders of magnitude.

Typically, when the in use concentration is a wet use (i.e. wet fabric or hair) increasing the concentration in product by three orders of magnitude over the calculated neat product concentration should suffice. For non-wet applications (i.e. deodorant, air care device) increasing the concentration in product by five orders of magnitude over the calculated neat product concentration should suffice.

For example, 0.015% of the Example Accord will deliver an equilibrium wet fabric and/or hair headspace of approximately 0.024 ppb (equivalent to about 7.4 ng/cf) and 0.056% of the Example Accord will deliver an equilibrium wet fabric and/or hair headspace of approximately 0.09 ppb (equivalent to about 27.7 ng/cf).

In a soft solid Antiperspirant context as an example, approximately 0.4% of the accord would be needed to ensure the concentration of the Example Accord is at least 7.4 ng/cf when it reaches the user's nose and approximately 1.5% of the accord would be needed to ensure the concentration of the Example Accord is at least 27.7 ng/cf when it reaches the user's nose.

Example Soft Solid Antiperspirant and Shampoo Formulas containing the required levels of the Example Accord are found below. The shampoo below is made by combining the ingredients in Table 13 in the amounts given. All materials are in weight percent of total formula.

TABLE 13

Shampoo formulas

| Ingredient | EXAMPLE SHAMPOO COMPOSITION | | |
|---|---|---|---|
| | I | II | III |
| Polyquaterium 76 [1] | 0.25 | 0.25 | 0.25 |
| Guar, Hydroxylpropyl Trimonium Chloride [2] | — | — | — |
| Guar, Hydroxylpropyl Trimonium Chloride [3] | — | — | — |
| Polyquaterium 6 [4] | — | — | — |
| Sodium Laureth Sulfate (SLE3S) [5] | 6 | 6 | 6 |
| Sodium Laureth Sulfate (SLE1S) [6] | — | — | — |
| Sodium Lauryl Sulfate (SLS) [7] | 7 | 7 | 7 |
| Silicone [8] | 0.5 | 0.5 | 0.5 |
| Gel Network [9] | — | — | — |
| Cocoamidopropyl Betaine [10] | 2.0 | 2.0 | 2.0 |
| Cocoamide MEA [11] | 0.85 | 0.85 | 0.85 |
| Ethylene Glycol Distearate [12] | 1.50 | 1.50 | 1.50 |
| Sodium Benzoate | 0.25 | 0.25 | 0.25 |
| Disodium EDTA | 0.13 | 0.13 | 0.13 |
| Example Accord | 0.015 | 0.025 | 0.056 |
| 5-Chloro-2-methyl-4-isothiazolin-3-one, Kathon CG | 0.0005 | 0.0005 | 0.0005 |
| Sodium Chloride/ Ammonium Xylene Sulfonate | Adjust viscosity to 2000 to 10,000 cps | Adjust viscosity to 2000 to 10,000 cps | Adjust viscosity to 2000 to 10,000 cps |
| Citric Acid or Sodium Citrate Dihydrate | Adjust to pH 5 to 7 | Adjust to pH 5 to 7 | Adjust to pH 5 to 7 |
| Water | Balance | Balance | Balance |

[1] Mirapol AT-1, Copolymer of Acrylamide (AM) and TRIQUAT, MW = 1,000,000; CD = 1.6 meq./gram; Supplier Rhodia
[2] Jaguar C500, MW-500,000. CD = 0.7, supplier Rhodia
[3] Jaguar C17, supplier Rhodia
[4] Mirapol 100S, supplier Rhodia
[5] Sodium Laureth Sulfate, supplier P&G
[6] Sodium Laureth Sulfate, supplier P&G
[7] Sodium Lauryl Sulfate, supplier P&G
[8] Dimethicone Fluid, Viscasil 330M; 30 micron particle size; supplier Momentive Silicones Each version of the shampoo (versions I, II and III) is used by consumers and the consumer's stress level, as measured by the bio-markers and methods disclosed in the present specification, is reduced.

The Soft Solid Antiperspirant below is made by combining the ingredients in Table 14 in the amounts given. All materials are in weight percent of total formula.

TABLE 14

Soft Solid Antiperspirant Formulas

| Ingredient | EXAMPLE SOFT SOLID ANTIPERSPIRANT COMPOSITION | | |
|---|---|---|---|
| | I | II | III |
| Aluminum Zirconium Trichlorohydrex Glycine Powder | 26.5 | 26.5 | 26.5 |
| Cyclopentasiloxane | QS. | Q.S. | Q.S. |
| Dimethicone | 5 | 5 | 5 |
| Tribehenin | 4.5 | 4.5 | 4.5 |
| C 18-36 acid triglyceride | 1.125 | 1.125 | 1.125 |
| PPG-14 Butyl Ether | 0.5 | 0.5 | 3.5 |

TABLE 14-continued

Soft Solid Antiperspirant Formulas

| Ingredient | EXAMPLE SOFT SOLID ANTIPERSPIRANT COMPOSITION | | |
| --- | --- | --- | --- |
| | I | II | III |
| White Petrolatum | 3 | 3 | 3 |
| Example Accord | 0.4 | 0.9 | 1.5 |
| Cyclopentasiloxane | Balance to 100% | Balance to 100% | Balance to 100% |

Each version of the soft solid antiperspirant (versions I, II and III) is used by consumers and the consumer's stress level, as measured by the bio-markers and methods disclosed in the present specification, is reduced.

REFERENCES

1. Nater, U. M., Rohleder, N. (2009). Salivary alpha-amylase as a non-invasive biomarker for the sympathetic nervous system: Current state of research. Psychoneuroendocrinology, 34(4), 486-96.
2. van Stegeren, A., Rohleder, N., Everaerd, W., Wolf, O. T. (2006). Salivary alpha amylase as marker for adrenergic activity during stress: Effect of betablockade. Psychoneuroendocrinology, 31(1), 137-41.
3. Proctor, G. B., Carpenter, G. H. (2007). Regulation of salivary gland function by autonomic nerves. Auton Neurosci, 133(1), 3-18.
4. Keller, P. S., El-Sheikh, M., Vaughn, B., Granger, D. A. (2009). Salivary alpha-amylase as a longitudinal predictor of children's externalizing symptoms: Respiratory sinus arrhythmia as a moderator of effects. Psychoneuroendocrinology, 34(5), 633-43.
5. Gordis, E. B., Margolin, G., Spies, L., et al. (2010). Interparental aggression and parent-adolescent salivary alpha amylase symmetry. Physiol Behav, 100(3), 225-33.
6. Gordis, E. B., Granger, D. A., Susman, E. J., Tickett, P. K. (2008). Salivary alpha amylase-cortisol asymmetry in maltreated youth. Horm Behav, 53(1), 96-103.
7. Granger, D. A., Kivlighan, K. T., El-Sheikh, M., et al. (2007). Salivary α-amylase in biobehavioral research: Recent developments and applications. Ann N Y Acad Sci, 1098, 122-44.)
8. Nishimura, Nobuhiro; Niwa, Takeshi. (2009) Influence of neroli flavor on psychological stress load Aromatopia (2009), 95, 12-14.
9. Komori, Teruhisa (2008) Anti-stress and antidepressant effects of fragrances and autonomic nervous system. Aroma Research (2008), 9(3), 202-207.
10. Sawabe, Akiyoshi; Tojima, Takeshi; Nakatani, Taichi; Takeda, Ryuji; Iida, Akira; Takahashi, Kazuhiro; Yamaguchi, Takashi. (2012) About the estrogenic activity and the stress reduction and a relaxation effect of odor after stress loading. Aroma Research (2012), 13(1), 58-63.
11. Fukui, Hajime (2010) Influence of odor on the human body—human pheromone, steroids and behavioral endocrinological study. Aroma Research (2010), 11(1), 79-83.
12. Fukui, Hajime; Komaki, Ryoichi; Okui, Miho; Toyoshima, Kumiko; Kuda, Kiyoto (2007) The effects of odor on cortisol and testosterone in healthy adults. Neuroendocrinology Letters (2007), 28(4), 433-437.
13. Bensafi, M.; Rouby, C.; Farget, V.; Bertrand, B.; Vigouroux, M.; Holley, A. (2002) Autonomic Nervous System Responses to Odours: the Role of Pleasantness and Arousal. Chemical Senses (2002), 27(8), 703-709.
14. Warrenburg, Stephen (2002) Measurement of emotion in olfactory research. ACS Symposium Series (2002), 825 (Chemistry of Taste), 243-260.
15. Vernet-Maury, Evelyne; Alaoui-Ismaili, Ouafae; Dittmar, Andre; Delhomme, Georges; Chanel, Jacques (1999) Basic emotions induced by odorants: a new approach based on autonomic pattern results. Journal of the Autonomic Nervous System (1999), 75(2,3), 176-183.
16. U.S. Patent Publication No. 2014/0194338 to Behan et al.
17. U.S. Patent Publication No. 2012/0015058 to Lee et al.
18. Korean Patent Application No. KR 2004056622 to Kim et al.
19. U.S. Patent Publication No. 2004/0033279 to Warrenberg et al.
20. Wong I S, Ostry A S, Demers P A, Davies H W. (2012) Job strain and shift work influences on biomarkers and subclinical heart disease indicators: a pilot study. J Occup Environ Hyg. 9(8):467-77.
21. Taverniers J, De Boeck P. (2014). Force-on-Force handgun practice: an intra-individual exploration of stress effects, biomarker regulation, and behavioral changes. Hum Factors. March; 56(2):403-13.
22. Feicht T, Wittmann M, Jose G, Mock A, von Hirschhausen E, Esch T. (2013). Evaluation of a seven-week web-based happiness training to improve psychological well-being, reduce stress, and enhance mindfulness and flourishing: a randomized controlled occupational health study. Evid Based Complement Alternat Med. 2013:676953. Epub 2013 Dec. 31.
23. Zauber H1, Mosler S, von Heßberg A, Schulze W X. (2012) Dynamics of salivary proteins and metabolites during extreme endurance sports—a case study. Proteomics. July; 12(13):2221-35.
24. Soo-Quee Koh D, Choon-Huat Koh G. (2007). The use of salivary biomarkers in occupational and environmental medicine. Occup Environ Med. March; 64(3):202-10.

Although the presently disclosed subject matter and its advantages have been described in detail, it should be understood that various changes, substitutions and alterations can be made herein without departing from the spirit and scope of the application as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods, or steps.

Patents, patent applications publications product descriptions, and protocols are cited throughout this application the disclosures of which are incorporated herein by reference in their entireties for all purposes.

What is claimed is:
1. A method of reducing or inhibiting a stress response in a subject in need thereof, comprising administering a fra- grance composition in an amount effective to reduce or inhibit a stress response to stress stimuli, wherein the fragrance comprises:
- a) at least one musk accord; and
- b) one or more bases, solvents and combinations thereof, and wherein the at least one musk accord comprises:
- i) at least one musk compound selected from the group consisting of 1,4-dioxacycloheptadecane-5,17-dione, (12E)-1-oxacyclohexadec-12-en-2-one, 5-cyclohexadecen-1-one, and 3-methyl-5-((1R)-2,2,3-trimethylcyclopentyl)pentan-2-one; and
- ii) at least two musk compounds selected from the group consisting of 1,4-dioxacyclohexadecane-5,16-dione, 16-oxacyclohexadecan-1-one, 11-oxa-16-hexadecanolide, (1R,6S)-ethyl 2,2,6-trimethylcyclohexanecarboxylate, and 1-(3,3-dimethylcyclohexyl)ethyl acetate.

2. The method of claim 1, wherein the musk accord comprises (12E)-1-oxacyclohexadec-12-en-2-one.

3. The method of claim 1, wherein at least one musk accord comprises:
- i) a first musk compound 1,4-dioxacycloheptadecane-5,17-dione;
- ii) a second musk compound selected from the group consisting of (12E)-1-oxacyclohexadec-12-en-2-one, 5-cyclohexadecen-1-one and 3-methyl-5-((1R)-2,2,3-trimethylcyclopentyl)pentan-2-one; and
- iii) a third musk compound selected from the group consisting of 1,4-dioxacyclohexadecane-5,16-dione, 16-oxacyclohexadecan-1-one, 11-oxa-16-hexadecanolide, (1R,6S)-ethyl 2,2,6-trimethylcyclohexanecarboxylate, and 1-(3,3-dimethylcyclohexyl)ethyl acetate.

4. The method of claim 1, wherein the at least one musk accord comprises 1,4-dioxacycloheptadecane-5,17-dione, (12E)-1-oxacyclohexadec-12-en-2-one, 1,4-dioxacyclohexadecane-5,16-dione, 16-oxacyclohexadecan-1-one, and 11-oxa-16-hexadecanolide.

5. The method of claim 1, wherein the at least one musk accord comprises (1R,6S)-ethyl 2,2,6-trimethylcyclohexanecarboxylate, 5-cyclohexadecen-1-one, and 1,4-dioxacycloheptadecane-5,17-dione.

6. The method of claim 1, wherein the at least one musk accord comprises a fragrance compound selected from the group consisting of raspberry ketone, linalool, linalyl acetate, and combinations thereof.

7. The method of claim 1, wherein the at least one musk accord is present in the fragrance composition in an amount of from about 1% to about 100% by the weight of fragrance composition.

8. The method of claim 1, wherein the at least one musk accord is present in the fragrance composition in an amount of at least about 5%.

9. The method of claim 1, wherein the at least one musk accord is present in the fragrance composition in an amount of at least about 10%.

10. The method of claim 1, wherein the at least one musk accord is present in the fragrance composition in an amount of at least about 20%.

11. The method of claim 1, wherein the fragrance composition can be administered to the subject before, during or after exposure to the stress stimuli.

12. The method of claim 1, wherein the stress response is change in at least one hormone in the subject.

13. The method of claim 12, wherein the at least one hormone is selected from the group consisting of cortisol, alpha amylase, and combinations thereof.

* * * * *